United States Patent
Madsen, II et al.

(10) Patent No.: US 11,053,527 B2
(45) Date of Patent: Jul. 6, 2021

(54) FERMENTATIVE PROCESS FOR THE MANUFACTURE OF MALTOSYL-ISOMALTOOLIGOSACCHARIDES (MIMO)

(71) Applicant: ISOThrive Inc., Healdsburg, CA (US)

(72) Inventors: Lee Madsen, II, Manassas, VA (US); Jack Oswald, Healdsburg, CA (US); Sarah Stanley, Arlington, VA (US)

(73) Assignee: ISOThrive Inc., Healdsburg, CA (US)

( * ) Notice: Subject to any disclaimer, the term of this patent is extended or adjusted under 35 U.S.C. 154(b) by 44 days.

(21) Appl. No.: 16/092,362

(22) PCT Filed: Apr. 11, 2017

(86) PCT No.: PCT/US2017/027013
§ 371 (c)(1),
(2) Date: Oct. 9, 2018

(87) PCT Pub. No.: WO2017/180626
PCT Pub. Date: Oct. 19, 2017

(65) Prior Publication Data
US 2019/0093139 A1    Mar. 28, 2019

Related U.S. Application Data

(60) Provisional application No. 62/320,873, filed on Apr. 11, 2016.

(51) Int. Cl.
| | |
|---|---|
| *C12P 19/18* | (2006.01) |
| *C12P 19/04* | (2006.01) |
| *C12N 1/20* | (2006.01) |
| *C07H 3/06* | (2006.01) |
| *C07H 1/00* | (2006.01) |
| *C08B 37/00* | (2006.01) |

(52) U.S. Cl.
CPC ............... *C12P 19/18* (2013.01); *C07H 1/00* (2013.01); *C07H 3/06* (2013.01); *C08B 37/0006* (2013.01); *C12N 1/20* (2013.01); *C12P 19/04* (2013.01); *C12Y 204/01005* (2013.01)

(58) Field of Classification Search
CPC .............. A61K 2300/00; A61K 35/741; A61K 35/744; A61K 35/747; A61K 31/715; A61K 9/08; A61K 9/14; A61K 35/74; A61K 38/00; A61K 38/16; A61K 38/164; A61K 31/702; A61K 31/717; A61K 31/718; A61K 31/732; A61K 31/733; A61K 31/736; A61K 35/66; C12P 19/04; C12P 19/18; A23L 33/125; A01N 63/10; A61P 35/00; A61P 1/00; A61P 3/00; A61P 5/00; C07H 1/00; C07H 3/06; C07H 1/06; C07K 14/315; C08B 37/0006; C12N 1/20; C12Y 204/01005; C12M 47/02; C12M 47/10; C12M 47/12; C12Q 1/04; C12Q 1/68; C12Q 1/689
See application file for complete search history.

(56) References Cited

FOREIGN PATENT DOCUMENTS

| WO | WO-2016029198 A1 | 2/2016 |
|---|---|---|
| WO | WO-2017180626 A1 | 10/2017 |

OTHER PUBLICATIONS

Lee et al, "Optimized substrate concentrations for production of long-chain isomaltooligosaccharides using dextransucrase of Leuconostoc mesenteroides B-512F". J. Microbiol. Biotechnol. (2008), 18(6), pp. 1141-1145. (Year: 2008).*
"International Application Serial No. PCT US2017 027013, International Preliminary Report on Patentability dated Oct. 25, 2018", 6 pgs.
"European Application Serial No. 17782981.9, Extended European Search Report dated Nov. 7, 2019", 10 pages.
Cho, Seung Kee, "Simple Synthesis of Isomaltooligosaccharides during Sauerkraut Fermentation by Addition of Leuconostoc Starter and Sugars", Food Science and Biotechnology; vol. 24, No. 4, (Aug. 31, 2015), pp. 1443-1446.
Ndegwa, Henry Maina, "NMR spectroscopic analysis of exopolysaccharides produced by Leuconostoc citreum and Weissella confusa", Carbohydrate Research, vol. 343, (2008), pp. 1446-1455.
Qiao, Shi, "Optimization of isomaltooligosaccharide size distribution by acceptor reaction of Weissella confusa dextransucrase and characterization of novel alpha-(I-2)-branched isomaltooligosaccharides", Journal of Agricultural and Food Chemistry vol. 64, (Apr. 6, 2016), pp. 3276-3286.
Shukla, Shraddha, "Weissella confusa Cab3 dextransucrase: properties and in vitro synthesis of dextran and glucooligosaccharides", Carbohydrate Polymers, vol. 101, (2014), pp. 554-564.
Chung, Chang-Ho, "A potential nutraceutical from Leuconostoc mesenteroides B-742 (ATCC 13146) production and properties", LSU Doctoral Dissertations, [Online] Retrieved from the Internet: <http//digitalcommons.lsu.edu/gradschool_dissertations/464>, 2002.
"International Application Serial No. PCT/US2017/027013, International Search Report dated Jul. 20, 2017", 2 pgs.
"International Application Serial No. PCT/US2017/027013, Written Opinion dated Jul. 20, 1017", 4 pgs.
"European Application Serial No. 17782981.9, Communication Pursuant to Article 94(3) EPC dated Sep. 25, 2020", 5 pgs.
"European Application Serial No. 17782981.9, Response filed Apr. 22, 2020 to Extended European Search Report dated Nov. 7, 2019", 14 pgs.
"European Application Serial No. 17782981.9, Response filed Mar. 29, 2021 to Communication Pursuant to Article 94(3) EPC dated Sep. 25, 2020", 137 pgs.

* cited by examiner

*Primary Examiner* — Deborah K Ware
(74) *Attorney, Agent, or Firm* — Schwegman Lundberg & Woessner, P.A.

(57) ABSTRACT

Described herein are efficient, low cost methods for making prebiotics that contain maltosyl-isomaltooligosaccharides (MIMOs), as well as compositions made by such methods.

11 Claims, 5 Drawing Sheets

FERMENTATIVE PROCESS FOR THE MANUFACTURE OF MALTOSYL-ISOMALTOOLIGOSACCHARIDES (MIMO)

PRIORITY

This application is a U.S. national stage application filed under 35 U.S.C. § 371 from International Application Serial No. PCT/US2017/027013, filed on Apr. 11, 2017, and published as WO 2017/180626 on Oct. 19, 2017, which claims benefit of priority from U.S. Provisional Patent Application Ser. No. 62/320,873, filed on Apr. 11, 2016, which applications are hereby incorporated by reference in their entireties.

BACKGROUND

With the rise of antibiotic resistant bacteria, elimination of antibiotics use in livestock has become a necessity. Traditionally, antibiotics have been used to keep livestock healthy and free of human pathogens including *Salmonella* (*typhimurium*), *Campylobacter* (*jejuni*), and *Escherichia* (*coli*) spp. (Swartz. M., *Clin. Infect. Dis.*, 2002, 34:S111-S112; Bergeron, C. R. et al., *Emerging Infectious Diseases*, 2012, 18:415-421). However, the widespread application of antibiotics in cattle, swine and chickens can lead to the creation of antibiotic resistant bacterial species. This has been noted in chickens, especially where *Salmonella* spp. were found to be particularly resistant to oxytetracycline (Evangelisti. D. G. et al., *Antimicrob. Agents Chemother.*, 1975, 8:664-672). The same antibiotics used in animal feed are also used to treat disease in man (Phillips, I. et al., *J. Antimicrob. Chemother.*, 2004, 53:28-52) leading to the spread of resistant bacteria in human populations.

Prebiotics offer a viable alternative to antibiotics in feedstock. In both humans and animals, it has been shown that host health is closely related to the gut microbiota (Stanley, D. et al., *Appl. Microbiol. Biotechnol.* 2014, 98:4301-4310). A healthy and balanced microbiome acts as a barrier to invading pathogens and produces metabolic substrates (short-chain fatty acids, in particular) that support growth of intestinal epithelial cells, improving uptake of nutritive calories, vitamins, minerals, etc. The most well documented prebiotics are fructooligosaccharides and derivatives thereof, but there are other non-digestible oligosaccharides that have been shown to have similar results, and therefore, so should an isomaltooligosaccharide (Hu, Y. et al., *Lett. Appl. Microbiol.*, 2013, 57:108-114).

However, some of the best prebiotics are costly to manufacture, and numerous animals would need to be treated to reduce the incidence of antibiotic resistance. Hence, the manufacture and use of such prebiotics for animals is currently prohibitively expensive.

SUMMARY

The invention provides efficient, low cost methods for making prebiotics that contain maltosyl-isomaltooligosaccharides (MIMOs). These methods involve growth of a microorganism that can produce one or more dextransucrase enzymes that catalyze the polymerization of glucose (e.g., from a sucrose feedstock) in the presence of an acceptor molecule, which can be a sugar such as maltose. As described herein, rather than using food-grade sucrose and maltose, non-food grade sources of sucrose and maltose can be employed. The resulting composition contains a distribution of MIMOs that is similar to a food-grade prebiotic described in PCT/US2017/013957 filed Jan. 18, 2017 and U.S. Provisional Application 62/280,026, filed Jan. 18, 2016 by Madsen and Oswald, which are both incorporated herein by reference in their entireties.

The processes and compositions described herein demonstrate that a prebiotic containing a useful population of MIMOs (with a distribution of MIMOs oligosaccharides similar to the food-grade product, IsoThrive™) can be made as an additive for animal feed at significantly lower cost by adapting the manufacturing process to use sucrose-containing and maltose-containing feedstocks that are not food-grade. The differences in the MIMO compositions so produced do not negatively affect the action of the product. However, the MIMO compositions made by the processes described herein are discrete from the food grade MIMO, and can contain some different components. The compositions provided herein are also significantly different from other commercial prebiotics based on formulations containing MIMO of various types.

These MIMO compositions described herein can therefore be used as effective prebiotics for animals such as birds, mammals, and fish.

DETAILED DESCRIPTION

Figure 1:
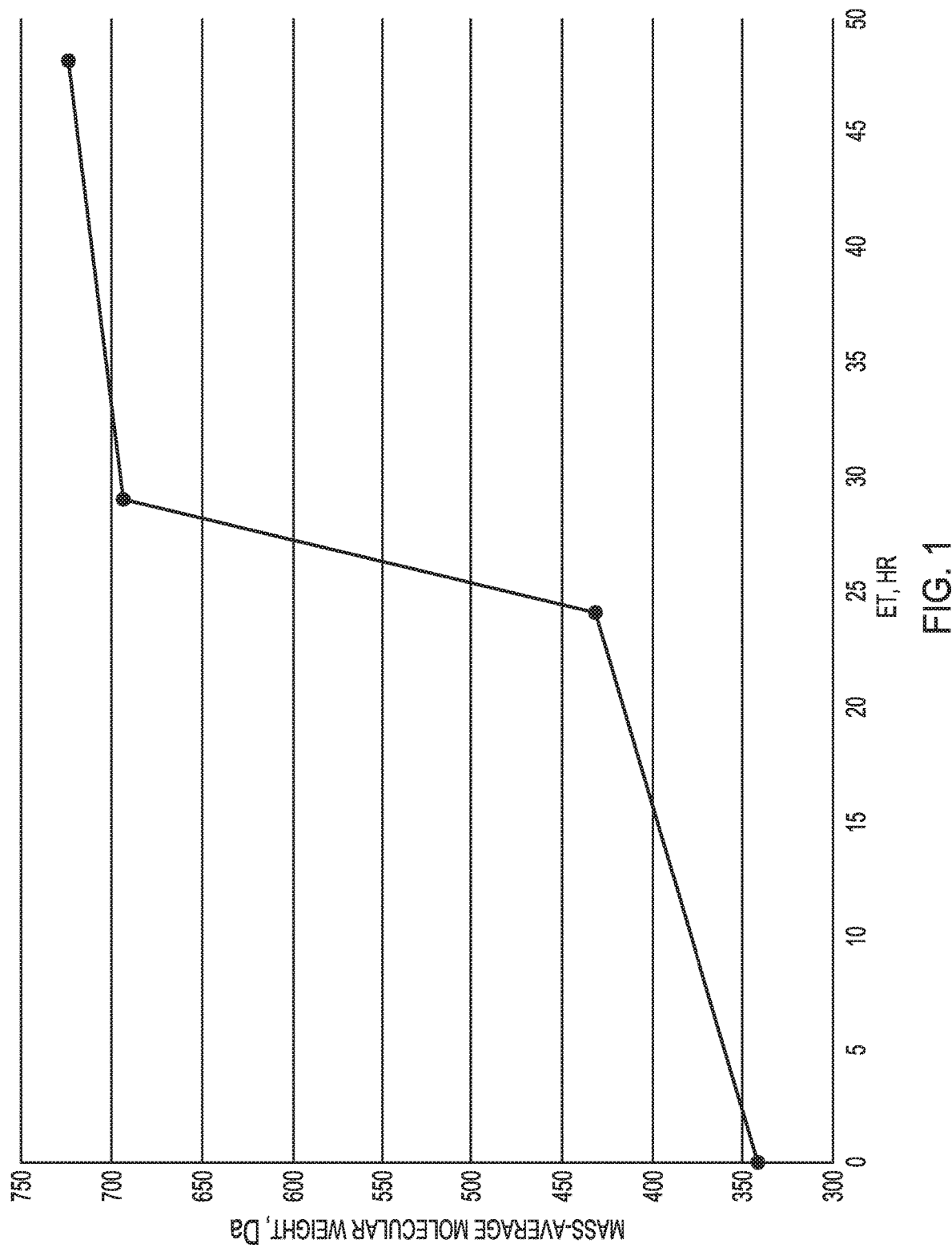
FIG. 1 illustrates the evolution of mass-average molecular weight distribution (MWD) of maltosyl-isomaltooligosaccharides (MIMOs) over time, where the MIMOs were formed via fermentation of Satin Sweet™ high-maltose syrup and refined white sugar (sucrose) from sugar cane. The MWD is similar to that observed when using high-purity maltose monohydrate at a similar sucrose:maltose ratio.

The application describes efficient, low cost methods for making prebiotics that contain maltosyl-isomaltooligosaccharides (MIMOs). Such prebiotics are useful as a viable alternative to antibiotics for administration to animals. The MIMO prebiotic compositions described herein help generate a healthy and balanced microbiome within the digestive system of animals, including mammals, birds and fish. For example, such a microbiome acts as a barrier to invading pathogens and produces metabolic substrates (short-chain fatty acids, for example) that support the growth of intestinal epithelial cells, improve the uptake of nutritive calories, vitamins, and minerals, and provide beneficial immunomodulation. For example, administering a probiotic (e.g., containing *Lactobacillus salivarius*) to one-day old chicks can protect chicks from disease for a time. Such a one-day administration of a probiotic plus administration of low levels of the compositions made as described herein over time provides sustained protection. If animals have a reasonably healthy and balanced microbiome within their digestive systems then administration of the compositions described herein can maintain and even improve the functioning of such microbiomes and of the animals' digestive systems.

Maltosyl-Isomaltooligosaccharides (MIMOs)

"Maltosyl-isomaltooligosaccharides," or MIMOs, refer to oligosaccharides, isomaltooligosaccharide glucans, of less than 30 (sometimes less than 10) degrees of polymerization comprised of α-(1→6) linkages terminated via an α-(1→4) linkage to the reducing-end. The α-(1→4) terminal group is comprised of maltose. Therefore maltosyl-isomaltooligosaccharide, or MIMO (or IMOM/IMOG, as per IUPAC convention), is produced by an acceptor reaction, where the acceptor is typically either maltose or other isomaltooligosaccharide. An example of an MIMO with a single maltosyl linkage [—O-α-(1,4)-] at the reducing end is maltosyl-isomaltotriose, which has the following chemical structure:

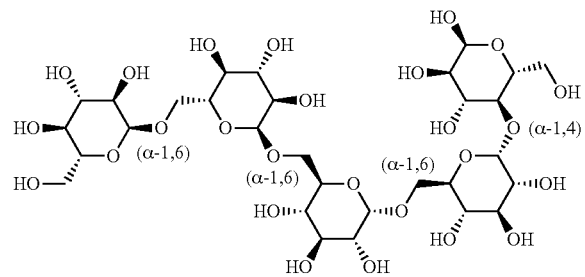

DP = 5

MIMOs can be generated by the methods described herein from a fermentation mixture that includes an impure source of a glucosyl donor (e.g. a raw sugar source of glucose or sucrose) and a sugar acceptor. Examples of sugar acceptors include sugar residues such as maltose, isomaltose, lactose, alpha methyl glucosides, α-d-glucopyranosyl-(1→5)-d-arabinonic acid, α-d-glucopyranosyl-(1→4)-d-glucitol, α-d-glucopyranosyl-(1→6)-d-glucitol, α-d-glucopyranosyl-(1→6)-d-mannitol, α-d-fructofuranosyl-β-d-fructofuranosyl-(1,2':2,3')-dianhydride, 1,5-anhydro-2-deoxy-d-arabino-hex-1-enitol ('d-glucal'), and combinations thereof. In many cases, maltose or isomaltose are good acceptors The methods for generating MIMOs can involve use of a fermentation mixture that contains a dextransucrase-producing microorganism in an aqueous culture medium, where the medium can have a ratio of sucrose to maltose ranging, for example, from about 0.20 to 7.0, or from about 0.5 to 4.0, or from 2.0 to about 4.0 at the time of inoculation, and where the sucrose and/or the maltose can be impure sucrose and/or impure maltose. The fermentation mixture is incubated for a time and under conditions sufficient to generate a composition that contains maltosyl-isomaltooligosaccharide with a mass average molecular weight distribution of about 650 to 1000 daltons, or 650 to 1500 daltons, or 650-2000 daltons.

The MIMOs are prepared using impure sources for sucrose and maltose. An "impure" source of sucrose or maltose does not contain detectable levels of toxic compounds. For example, the MIMOs do not contain toxic compounds, heavy metals, or toxic materials detectable by HPAEC-PAD, HPLC, inductively coupled plasma mass spectrometry (ICP-MS), or HPLC-RID.

However, such impure sources can contain less than 100% sucrose or maltose. For example, the impure sources of sucrose or maltose can contain less than 99%, or less than 99.5%, or less than 98%, or less than 98.5%, or less than 98%, or less than 97%, or less than 96%, or less than 95%, or less than 90%, or less than 85%, or less than 80%, or less than 75%, or less than 70%, or less than 67%, or less than 66%, or less than 65% sucrose or maltose.

The impure sources of sucrose and maltose typically do contain more than 30%, or more than 35%, or more than 40%, or more than 45%, or more than 50%, or more than 55%, or more than 60%, or more than 63%, or more than 65%, or more than 66%, or more than 68%, or more than 70%, or more than 75%, or more than 80%, or more than 85%, or more than 90%, or more than 93%, more than 94%, or more than 95%, or more than 96%, or more than 97%, or more than 97.5%, or more than 98%, or more than 98.5% sucrose or maltose.

In some cases the purity of the sucrose source is greater than the purity of the maltose. For example, the non-food-grade sucrose can have more than 90%, or more than 93%, more than 94%, or more than 95%, or more than 96%, or more than 97%, or more than 97.5%, or more than 98%, or more than 98.5% sucrose. In contrast the source of non-food-grade maltose can have less than 95%, or less than 90%, or less than 85%, or less than 80%, or less than 75%, or less than 70%, or less than 67%, or less than 66%, or less than 65% maltose, or less than 60%, or less than 55%, or less than 50%, or less than 45%, or less than 40%, or less than 35%, or less than 30% maltose.

Impurities in the sources of maltose can include water, dextrose, maltodextrin-type oligosaccharides and their higher polymers, e.g. starch, and mixtures thereof. For example, the impure (e.g. non-food-grade) sources of maltose can include starch and/or dextran, and mixtures thereof.

In addition, the non-food-grade source of maltose can also contain maltodextrin oligosaccharides as impurities.

The impure source of sucrose can also include water, dextrose, fructose, maltose, isomaltose, oligosaccharides of maltose, oligosaccharides of isomaltose, polymers of maltose, polymers of isomaltose, and/or combinations thereof. The impure source of sucrose can also include maltose, isomaltose, and/or oligosaccharides containing sucrose or maltose as impurities.

Although the fermentation methods described herein can efficiently generate MIMOs from a variety of impure sources of sucrose and an acceptor (e.g., maltose), it is advisable to evaluate the composition of these non-food-grade sources of sucrose and maltose so that the amounts used can be adjusted within the fermentation mixture to provide a ratio of sucrose to maltose ranging from about 0.20 to 7.0, or from about 0.5 to 4.0, or from 2.0 to about 4.0 at the time of inoculation.

Examples of impure (e.g., non-food-grade) sources of sucrose include, for example, raw sugar (e.g., commercially available from sugar cane), molasses, syrup from sugarcane, sweet sorghum and/or energy cane, grasses, beet sugar, beet molasses, sugar beet greens, maple syrup, algal sources (e.g. *Neochloris oleoabundans*), energy cane, and/or any combinations thereof. Such impure sources of sucrose can be obtained from various parts of the plants including leaves, greens, tops, stalks, seeds, or combinations thereof. In some cases, the sucrose may be obtained from the entire plant. Energy cane (*Sacharum spontaneum*) is sugarcane that has been bred and selected for biomass or fiber production over sucrose Examples of impure (e.g., non-food-grade) sources of maltose include, for example, maltose syrup, high maltose syrup, malt, saccharified starch, and combinations thereof. The starch can include corn/maize starch, potato starch, tapioca starch, wheat starch, oat starch, millet/sorghum starch, rice starch, arrowroot starch, taro starch, kudzu starch, yam starch, and/or any combination thereof.

The source of maltose used for the fermentation process (e.g., Satin Sweet™) can contain some glucose. For example, the sources of maltose can include about 0.1 to about 15% glucose, or about 0.1 to about 12% glucose, or about 0.1 to about 10% glucose, or about 0.1 to about 5% glucose, or about 0.2% to about 4% glucose, or about 0.5% to about 3% glucose. The sources of maltose can include oligosaccharides. For example, the non-food-grade sources of maltose can include oligosaccharides with about 3 to about 8 sugar units.

In some cases, the source of maltose for a non-food-grade can include Satin Sweet™, which typically has at least 50% maltose, or at least 60% maltose. An example of a composition of one batch of Satin Sweet™, which can be used as a source of maltose, has the following composition:

| | |
|---|---|
| Brix g/100 g DS | 82.7 |
| glucose, %/brix | 2.21 |
| maltose, %/brix | 65.70 |
| DP 3, %/brix | 16.24 |
| DP 4, %/brix | 2.29 |
| DP 5, %/brix | 0.76 |
| DP 6, %/brix | 0.39 |
| DP 7, %/brix | 0.09 |

The terms DP 3, DP 4, DP 5, DP 6, and DP 7 in the list above refer to maltodextrins with different degrees of polymerization (DP 3-7).

More complex impure sources of maltose, such as starch, can be treated to release maltose. For example, starch can be incubated with α-amylase, with or without added isoamylase, pullalanase, and/or dextranase to saccharify the starch, and thereby release maltose. Such incubation can be performed until the brix of the incubation mixture indicates that a majority of the maltose has been released from the starch. The extent of saccharification can be confirmed by HPAEC-PAD/HPLC-RID analysis prior to use in fermentation. The resulting maltose product can also be filtered and/or concentrated before use in the fermentation process.

Described herein are three examples detailing fermentations using (1) Substitution of maltose monohydrate (>95%) with 65% maltose syrup, (2) Substitution of maltose monohydrate (>95%) with 65% maltose syrup and substitution of refined white sugar with a commercial raw sugar product, and (3) Substitution of maltose monohydrate (>95%) with saccharified potato starch to demonstrate the flexibility that is possible with respect to feedstock relative to a consistent MIMO product distribution.

Fermentation is a reliable method for industrial manufacture of reproducible compositions of MIMOs. The size and composition of the product MIMOs may be closely controlled during fermentation. Upon start-up of the fermentation process, the entire equipment system can be flushed, cleaned and sterilized. A fermentation tank can then be charged with media components (e.g., with vitamins, sulfates, phosphates, salts and other materials used for bacterial growth such as those media recommended by ATCC for use in growing the microorganism being cultured, including for example DIFCO® dehydrated culture media and ingredients) and with sucrose and maltose in a defined ratio. In some cases, any complex, chemically defined, or rich media demonstrated to facilitate fermentation can be used, including media that contain corn steep liquor/solids, for example, in place of yeast extract, and other ingredients.

For example, a fermentation mixture can include sucrose (e.g., from a non-food-grade sucrose source), maltose (from a non-food-grade maltose source), manganese salt (e.g., $MnSO_4$ or $MnCl_2$), magnesium salt (e.g., $MgSO_4$ or $MgCl_2$), iron salt (e.g., $FeSO_4$ or $FeCl_2$), potassium salt (e.g., $KH_2PO_4$), sodium chloride, calcium salt (e.g., $CaCl_2$), and yeast extract.

Yeast extract is one source of nitrogen. Other nitrogen sources include corn steep liquor, peptone, tryptone, meat extract, casamino acids, casein, soy flour, and mixtures thereof. Corn steep liquor is a by-product of corn wet-milling. Typically, it is a viscous concentrate of corn solubles, which can contain amino acids, vitamins and minerals. Any such nitrogen sources can in some cases be used in the fermentation media.

Separately, an inoculum of the selected fermentation microorganism (in the preferred approach. ATCC 13146) can be grown until achieving to OD-1 (Optical Density or absorbance at 660 nm measurement of about 1 as measured by a UV-visible spectrophotometer). This inoculum can be added to the fermentation at a volume in the range of about 0.5% to about 20% of the volume of the fermentation, or about 1% to about 10% of the volume of the fermentation.

Any microorganism species capable of producing MIMOs, including *Leuconostoc mesenteroides*, may be utilized in the fermentation. For example, *L. citreum* ATCC 13146 may be used. This bacterium is known by other designations by those skilled in the art, including the designation *Leuconostoc* citreum ATCC 13146, the designation NRRL B-742, and the designation PWSA-*L. citreum* B742, the designation *Leuconostoc citreum* Farrow, and the designation *L. amelibiosum*. The bacterium *Leuconostoc mesentemides* subsp. *mesenteroides* (Tsenkovskii) van Tieghem (ATCC® 11449™), and/or *Leuconostoc citreum* NRRL B-1299, may also be employed. Other useful MIMO-producing microorganisms include, but not limited to, *Leuconostoc* spp (specifically *mesenteroides, citreum, gasicomitatum* and *kimchi*), *Weissella* spp (for example, *Weissella confusa*, such as NRRL #B 1064), *Lactococcus* spp., *Streptococcus* spp. (for example, *Streptococcus mutans*), *Lactobacillis* spp. (e.g., *Lactobacillis reuteri, Lactobacillis hilgardii, Lactobacillis acidophilus, Lactobacillis plantarum, Lactobacillis fermentum, Lactobacillis sakei*), *Pediococcus pentosaceus* spp. (e.g., *Pediococcus pentosaceus* (ATCC #33316), *Pediococcus acidilactici*), and certain mutant strains of *E. coli*.

Useful microorganisms may also be isolated from natural sources including, but not limited to, sourdough wild starter (the bioorganism mixture used in the production of sourdough bread) and *kimchi* (a traditional fermented Korean dish made of vegetables and seasonings). For many fermentation processes, *Leuconostoc citreum* ATCC 13146 is a useful microorganism.

Fed-batch conditions can be used to generate the MIMOs. Under fed-batch conditions, the process of generating MIMOs may run on a continuous, or semi-continuous basis. Staggered simultaneous batch fermentations can also be employed. Additional feedstock may be introduced to keep the fermentation going and to manage the sucrose:maltose ratio. The pH may be controlled during the extended fermentation at the same time by the addition of sodium hydroxide, lime, lime sucrate or another suitable base as described below. As the initial feedstock is consumed, additional feedstock, either sucrose or maltose, or both may be added to the culture medium. Such feedstock additions may be used (a) to maintain the initial fixed sucrose:maltose ratio or (b) to change the sucrose:maltose ratio as the fermentation proceeds. In one embodiment, sucrose is added separately from the maltose to achieve a specific sucrose:maltose ratio. In another embodiment, maltose is added separately from the sucrose as a means to adjust the sucrose:maltose ratio. Such maltose-only addition may also prevent its degradation from continuous contact with the strong base prior to addition to the culture. Either approach may be used to produce a first-order MIMO end product with the desired chemical composition.

The sucrose:maltose (S/M) ratio provides one type of control of product composition, in that it can affect or determine the degree of polymerization (DP) of the product distribution with respect to molecular weight.

The organism used for the fermentation can effect both the mass-average molecular weight and branching pattern of the product MIMO. For example, *Leuconostoc mesenteroides* B512F generally produces linear α-1,6 MIMO while *Leuconostoc citreum* NRRL B-1299 generally produces a mixture of linear α-1,6 and α-1,6 MIMOs with α-1,2 branched MIMO glucans. The organism(s) employed may also create a bimodal distribution of oligosaccharides (e.g., MIMOs) ranging from DP2 to DP30. Such a bimodal distribution, can include a first MIMO distribution that is comprised of mostly linear MIMO, and a second IMO distribution that can include branched MIMOs. The first MIMO pool can be made by organisms such as, for example, *Leuconostoc mesenteroides* NRRL B-512F, *Weissella confusa* NRRL B-1064, and the like. The second distribution that can include branched MIMOs can be made by organisms such as, for example, *Leuconostoc citreum* NRRL B-742, *Leuconostoc citreum* NRRL B-1299, and the like. Other organisms such as *Leuconostoc mesenteroides* NRRL B-1355 (or mixtures of other organisms with NRRL B-1355) can produce a distribution of alternating structures such as alternan. Alternan has two monosaccharides in its repeating unit, [Glc(α1-3)Glc(α1-6)], but it can also contain some Glc(al-3) branching.

Under batch conditions, the bacteria can be grown in a nutrient mixture (culture medium) suitable to support growth of the bacteria and, for example, a fixed ratio of sucrose:maltose at the time of inoculation.

Fermentation is allowed to continue, for example, until oligosaccharide production is complete. The oligosaccharide production is complete, for example, when the sucrose is exhausted. Additional fermentation time may result in the reorganization of the MIMOs by chemical recombination that can change the DP distribution. In some cases, longer chains are formed, possibly from continued residual enzyme activity. Continuation until fructose is converted to mannitol also simplifies purification of the final product. Removing the spent bacteria cells and other purification steps can then be carried out.

The sucrose:maltose ratio at the time of inoculation may range from about 0.20 to about 7.0, or from about 0.3 to about 6.0, or from about 0.5 to about 5.0, or from about 2.0 to about 4.5, or from about 2 from about 2.2 to about 4.3, or about 2.3 to about 4.0, or about 2.4 to about 4.0, or about 2.5 to about 3.75, or about 2.5 to about 3.5, or about 2.5 to about 3.0, or about 2.75. All of these sucrose:maltose ratios, or any ratio between about 0.2 to about 7.0, can be utilized in the process of the invention to provide commercially desirable product MIMOs for mammalian, avian, and/or piscine consumption, for example, via feed supplementation.

For example, in some cases *Weissella* spp (e.g., *Weissella confusa* B-1064) can function differently than *Leuconostoc citreum* (such as *Leuconostoc citreum* ATCC 13146, also called NRRL B-742). Use of *Leuconostoc citreum* may produce MIMOs with a mass average molecular weight distribution of about 780 Da when using a sucrose:maltose of about 2.75. However, use of *Weissella confusa* can produce a similar mass average molecular weight distribution when using a sucrose:maltose of about 2.00 (or less).

In addition to the fermentation microorganism and the sucrose:maltose (S/M) ratio, the conditions for fermentation can influence the yield of MIMOs. Such conditions include a temperature, pH, and a time of fermentation sufficient to generate a composition comprising maltosyl-isomaltooligosaccharide with a mass average molecular weight distribution of about 650 to 2000 daltons, or about 650 to about 1500, or about 900 to about 2000.

The temperature for fermentation can vary, for example, depending on the organism employed for fermentation. Temperatures that can be employed include those ranging from about 10° C. to about 50° C., or from about 15° C. to about 45° C., or from about 20° C. to about 40° C., or from about 22° C. to about 37° C., or from about 23° C. to about 33° C., or from about 25° C. to about 30° C., or at about 27° C. to about 29° C. The fermentation can, for example, be performed at a temperature around about 28° C.

The pH for fermentation can vary somewhat as well. For example, the pH of the fermentation mixture during fermentation can vary within the range of 4 to 8. The pH of the fermentation naturally drops from its starting pH as the fermentation organism grows in culture in the presence of an appropriate feedstock. Close control of the pH of the fermentation mixture during fermentation allows refinement of the product composition. For example, when the range of pH is about 6.5 to 5.5, the product composition bell curve shifts to higher DP as the pH decreases. Conversely, when the range of pH is about 6.0 to 7.0, the product composition bell curve shifts to lower DP as the pH increases. An optimum pH for most cell growth is about 6.5 to 6.8. However, the dextransucrase enzyme(s) utilized by *Leuconostoc* citreum ATCC 13146 perform optimally at a pH of 5.5±0.3. Optimum enzyme production and activity is in the range of 5.5 to 6.0. A desirable pH of 5.5 can be maintained by the addition of an alkaline material such as sodium hydroxide. The pH of the fermentation mixture can initially be adjusted to about pH 6.5 with 50% aqueous sodium hydroxide or 37% hydrochloric acid, and can be maintained at about pH 5.5 during the selected length of time for fermentation.

The fermentation can be carried out to completion within about 60 hours in broths containing less than 40% total sugars (e.g., a maximum of about 28%/brix), with the range of 18-35% total sugars being preferred.

In some cases, the overall production of MIMOs can be increased by a continuous addition of a sucrose/maltose feed in the desired ratio of sucrose to maltose. This increase in product output and composition can be done independently of pH control if pH control is accomplished by the addition of an alkaline material such as sodium or potassium hydroxide, or can be done in conjunction with pH control.

The fermentation mixture can be incubated for varying amounts of time. For example, fermentation mixture can be incubated for about 20 to about 120 hours, or for about 25 to about 100 hours, or about 30 to about 90 hours, or about 35 to about 80 hours, or about 40 to about 70 hours. In some cases, the fermentation mixture can be continued until no fructose is present, for example, a period of time of approximately 25 to 60 hours. In some cases, the fermentation mixture can be incubated indefinitely while adding at least one of the sucrose and the maltose to the fermentation mixture and removing maltosyl-isomaltooligosaccharide therefrom.

The cells can be separated from the broth by a variety of methods. For example, suitable methods for removing the bacterial cells include centrifugation, filtration or chemical clarification. In one embodiment, centrifugation is employed. Types of separation include continuous liquid or batch centrifugation, use of a horizontal decanter, cream separator/disc centrifugation, and/or chemical clarification followed by decantation and/or filtration. Types of filtration include, but are not limited to, ultrafiltration, microfiltration or gel filtration.

The fermentation broth may be rendered free of cells (via microfiltration, centrifugation, etc.) or not, prior to reduction in volume (e.g., via evaporation or vaporation) to yield either a syrup additive or to yield a form suitable for spray drying to yield a powdered material. For liquid additive forms, a crystallization step similar to that described by Madsen and Oswald (U.S. Ser. No. 62/280,026 filed Jan. 18, 2016) may be performed. For powdered additive forms, this step is not necessary.

In some cases, the cells used during fermentation can be left in the final composition. In other cases the cells can be removed. The final product can be employed as a prebiotic for administration to animals. For example, no further purification of the MIMO product is typically needed.

However, if desired, the fermentation broth containing the MIMOs can also be decolorized through the use of granular activated charcoal or powdered activated charcoal. Such decolorization can be performed at a temperature of about 70 to about 80° C. The activated charcoal can be removed by filtration. Alternatively, the MIMO product can be separated from the decolorized broth using pulsed or simulated moving bed chromatography at about 60 to about 65° C. The extract can then be concentrated as desired and undesired insoluble impurities can be removed, for example, through centrifugation or microfiltration. If desired, the product can then be spray dried or freeze dried if the intent is to yield a powdered product.

Suitable methods for decolorization include, but are not limited to, the use of activated carbon in powder or granular form, with or without pH buffering (e.g. magnesite), and may be performed in either batch or continuous (e.g. column) mode. Activated charcoal may also be used. A suitable powered carbon includes Carbochem CA-50 (Carbochem Inc., Wynnewood, Pa.) or an equivalent activated carbon. In batch mode, decolorizing carbon can be added at about 60 to about 70° C., the bulk mixture can be allowed to cool to a temperature of about 40° C., and after agitation a filter aid is added. The bulk mixture is filtered to yield decolorized liquor.

In continuous mode, the bulk cell-free fermentation liquor can be passed through a column charged with granulated activated carbon at about 65 to about 70° C. Once saturated, the carbon can be kilned or regenerated in-place via treatment with alkaline ethanol or equivalent (Bento). Examples of suitable filter aids include, but are not limited to, silicon dioxide, diatomaceous earth, diatomite, and kieselguhr. Suitable brand names include Celite® 545 (Sigma-Aldrich, St. Louis, Mo.) and Celatom® (Sigma-Aldrich). The grade of filter is selected according to the desired time for filtration to occur at an optimum rate, as finer grades will slow down the filtration significantly.

In some embodiments, the bulk of the side-product mannitol can be removed by concentrating the mixture and cooling it until crystallization occurs. The crystals may then be separated via decantation, filtration or use of a basket centrifuge. Alternatively, fractional precipitation of products can be done using organic solvents such as ethanol.

In another embodiment, the mannitol and the organic acids may be further removed by continuous or pulsed chromatography. For example, a chromatographic grade gel-type strong acid exchange (SAC) resin in calcium form (SAC-Ca) kept at 45-70° C. may be utilized. Two main fractions result from the chromatography: 1) MIMO plus acetic acid; and 2) mannitol plus lactic acid. Some lactic acid, formic acid, and/or some acetic acid may remain in the MIMO fraction after the completion of the chromatography without interfering with further processing.

If de-ashing is desirable, an anion exchange resin in partial free-base form may be used, for example, as described by Saska and Chen (U.S. Pat. No. 6,451,123). Alternatively, the MIMO product-containing fraction may be further purified by removal of any heavy metal ions present utilizing an acid/base combination of ion exchange resins. Example combinations include, but are not limited to, strong acid exchange (SAC), strong base anion exchange (SBA), strong acid cation exchange (SAC), weak base anion exchange (WBA), weak acid cation exchange (WAC), strong base anion exchange, mixed bed systems, and combinations thereof performed in series.

Compositions

The application describes compositions and methods for production thereof that include, for example, maltosyl-isomaltooligosaccharides with a mass average molecular weight distribution of about 650 to 1000 daltons, or 650 to 1500 daltons, or 650-2000 daltons. In some cases, the mass average molecular weight distribution of the maltosyl-isomaltooligosaccharides is about 730 to 850 daltons, or about 800-1200 daltons, or, 900-2000 daltons.

The maltosyl-isomaltooligosaccharides in the compositions generally contain more α-(1-6) glucosyl linkages than α-(1,2), α-(1,3), or α-(1,4) glucose linkages. For example, a composition of oligosaccharides (maltosyl-isomaltooligosaccharides) can include at least 50% of the oligosaccharides with α-(1,6) glucosyl linkages, or at least 52% with α-(1,6) glucosyl linkages, or at least 55% with α-(1,6) glucosyl linkages, or at least 60% with α-(1,6) glucosyl linkages, or at least 65% with α-(1,6) glucosyl linkages, or at least 70% with α-(1,6) glucosyl linkages, or at least 75% with α-(1,6) glucosyl linkages, or at least 80% with α-(1,6) glucosyl linkages, or at least 83% with α-(1,6) glucosyl linkages, or at least 85% with α-(1,6) glucosyl linkages, or at least 87% with α-(1,6) glucosyl linkages, or at least 88% with α-(1,6) glucosyl linkages, or at least 89% with α-(1,6) glucosyl linkages, or at least 90% with α-(1,6) glucosyl linkages. While all MIMOs will have one alpha-(1,4) glucosyl linkage, some of the maltosyl-isomaltooligosaccharides in the composition can optionally have one or more α-(1,4) glucosyl linkages, or one or more α-(1,2) glucosyl linkages, or one or more α-(1,3) glucosyl linkages. Hence, the maltosyl-isomaltooligosaccharides are generally linear α-(1,6) glucooligosaccharides, terminated via α-(1,4) glycosidic linkage to a glucose reducing end (maltosyl end). The maltosyl-isomaltooligosaccharides in the compositions generally have no more than about 40 glucose units, no more than about 35 glucose units, no more than about 30 glucose units, no more than about 28 glucose units, no more than about 25 glucose units, no more than about 23 glucose units, no more than about 20 glucose units, no more than about 18 glucose units, or no more than about 17 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units as detected by HPAEC-PAD or HPLC-RID.

The compositions can contain some fructose and/or mannitol. For example, in some cases the compositions can have more than 5%/brix mannitol, or more than 7%/brix mannitol, or more than 8%/brix mannitol, or more than 9%/brix mannitol as detected by refractive HPAEC-PAD or HPLC-RID. Generally, the amount of mannitol in the compositions is less than 40%/brix mannitol, or less than 35%/brix mannitol, or less than 30%/brix mannitol, or less than 28%/brix mannitol, or less than 26%/brix mannitol, or less than 25%/brix mannitol, as detected by HPAEC-PAD or HPLC-RID. For example, the compositions can have about 10%/brix to about 40%/brix mannitol, or about 20%/brix to about 40%/brix mannitol. Fructose may be present in similar quantities, typically ranging from about 0 to 40% brix, or about 0 to 30%/brix, or about 0 to 25% brix, or about 0 to 20% brix.

Although the compositions generated by the methods described herein can have the same content of MIMOs as the food-grade MIMOs described in U.S. Application Ser. No. 62/280,026, the compositions provided herein can have other ingredients. For example, the present compositions can have one or more acids that are not found in food grade MIMOs. Such acids can include one or more of the following: lactic acid, formic acid, and acetic acid. For example, the present compositions can have 0 to about 40% lactic acid or sodium lactate, or about 0.5 to about 15% lactic acid. The compositions described herein can, for example, have about 0 to about 10% acetic acid. In addition, the compositions described herein can, for example, have about 0 to about 0.5% formic acid. The present compositions may also contain between 0 and 17%/brix (up to about 2% w/w) of ethanol.

Furthermore, the compositions generated by the methods described herein may also contain maltodextrins (e.g., maltodextrins with DP 3-17), which can originate from incomplete saccharification of the maltose source. These maltodextrins will be specific for, and can be referenced to, the starting starch saccharificate. This serves as a means of easily differentiating food-grade from feed/animal-grade products, and provides traceability to the originating process, factory, lot number, and enzyme/starch-types employed.

The compositions can be liquid or dry compositions.

The concentration of the components in the composition so prepared can be liquid compositions, for example, at 10% brix to 75% brix, or at 20% brix to 75% brix, or at 40% brix to 75% brix, or at 59-68%/brix. In some instances, the composition can be a spray dried/lyophilized powder. The mass average molecular weight distribution (MWD) can, for example, be in the range of about 650 to 1000 daltons, or 650 to 1500 daltons, or 650-2000 daltons, or in the range of 730 and 900 daltons (mass average).

The compositions can have a degree of polymerization (DP) ranging from about DP 3 to about DP30, or about DP 3 to about DP 25, or about DP 3 to about DP 20, or about DP 3 to about DP 15. In some cases, the DP can be about DP 3 to about DP 12, or about DP 3 to about DP 10, or about DP 3 to about DP 9.

Examples of compositions that can be generated by the methods described herein include the following.

a) A composition generated with high-maltose syrup and sucrose as described in Example 1 contains MIMO (DP 3-DP 9); mannitol; fructose; sucrose; maltose; 1,4-DP 3 oligosaccharide(s); lactate; glycerol; formate; and acetate, where the values shown are given as %/brix, or % of refractive dry solids.

| Hr Incubation: | 29 | 48 |
|---|---|---|
| brix: | 20.0 | 19.8 |
| mannitol | 10.26 | 24.08 |
| fructose | 0.56 | 0.08 |
| sucrose | 4.08 | 1.25 |
| maltose | 2.63 | 3.11 |
| MIMO-DP 3 | 12.04 | 8.79 |
| MIMO-DP 4 | 21.87 | 20.14 |
| 1,4-DP3 | 6.61 | 6.80 |
| MIMO-DP 5 | 13.41 | 13.96 |
| MIMO-DP 6 | 4.18 | 5.25 |
| MIMO-DP 7 | 1.63 | 2.14 |
| MIMO-DP 8 | 0.00 | 0.87 |
| 1,4-DP4 | 2.51 | 2.80 |
| MIMO-DP 9 | 0.00 | 0.00 |
| lactate | 4.23 | 10.79 |
| glycerol | 0.05 | 0.13 |
| formate | 0.00 | 0.02 |
| acetate | 1.69 | 4.10 |
| TOTAL: | 91.04 | 104.30 |
| MIMO, %: | 53.13 | 51.14 |
| Purity, %: | 58.36 | 49.03 |
| MWD: | 693.21 | 723.72 |
| Yield %: | 67.30 | 55.98 | where 1,4-DP3, and 1,4-DP4 are maltodextrins.

b) A composition generated with high-maltose syrup and raw sugar as described in Example 2 contains MIMO (DP 3-DP 9); mannitol; fructose; sucrose; maltose; 1,4-DP 3 oligosaccharide(s); 1,4-DP 4 oligosaccharide (s); lactate; glycerol; and acetate, where the values shown are given as %/brix, or % of refractive dry solids.

| Variable | Final |
|---|---|
| brix: | 18.7 |
| mannitol | 22.49 |
| fructose | 0.02 |
| sucrose | 1.03 |
| maltose | 2.99 |
| MIMO-DP 3 | 6.88 |
| MIMO-DP 4 | 14.07 |
| 1,4-DP3 | 6.29 |
| MIMO-DP 5 | 12.18 |
| MIMO-DP 6 | 5.90 |
| MIMO-DP 7 | 2.33 |
| MIMO-DP 8 | 1.04 |
| 1,4-DP4 | 5.02 |
| MIMO-DP 9 | 0.00 |
| lactate | 16.03 |
| glycerol | 0.35 |
| formate | 0.00 |
| acetate | 4.39 |
| TOTAL: | 101.52 |
| MIMO, %: | 42.40 |
| Purity, %: | 41.77 |
| MWD: | 745.47 |
| Yield %: | 45.76 | c) A composition generated with high-maltose syrup and potato starch as described in Example 3 contains MIMO (DP 4-DP 9); mannitol; glucose; sucrose; maltose; panose; 1,4-DP 3 oligosaccharide(s); 1,4-DP 4 oligosaccharide(s); lactate; glycerol; formate; and acetate, where the values shown are given as %/brix, or % of refractive dry solids, and where the balance of the mass is primarily maltodextrin.

| %/brix | 48 Hr | Final |
|---|---|---|
| Brix | 25.5 | 26.2 |
| mannitol | 18.28 | 17.35 |
| glucose | 0.44 | 0.93 |
| fructose | 0.00 | 0.00 |
| sucrose | 2.93 | 2.84 |
| maltose | 1.95 | 2.72 |
| panose | 4.65 | 4.43 |
| MIMO-DP4 | 11.33 | 9.96 |
| 1,4-DP3 | 10.66 | 10.23 |
| MIMO-DP5 | 10.29 | 9.05 |
| MIMO-DP6 | 7.08 | 6.82 |
| MIMO-DP7 | 2.94 | 3.12 |
| MIMO-DP8 | 1.85 | 1.69 |
| 1,4-DP4 | 9.93 | 6.33 |
| MIMO-DP9 | 0.00 | 0.00 |
| MIMO-DP10 | 0.00 | 0.00 |
| lactic acid | 8.30 | 8.08 |
| glycerol | 0.24 | 0.23 |
| formic acid | 0.06 | 0.05 |
| acetic acid | 2.92 | 2.86 |
| MIMO | 38.15 | 35.07 |
| MO | 20.59 | 16.56 |
| Total | 93.86 | 86.70 |
| Purity | 40.64 | 40.45 |
| MWD | 795.82 | 790.16 |
| S/M | n/a | n/a |

The methods described herein can generate compositions with a broader range of MIMOs. For example, the compositions can contain MIMOs with a degree of polymerization up to and including DP30. Hence, the MIMOs can have DP range of about DP3 to about DP30, or about DP3 to about DP27, or about DP3 to about DP25, or about DP3 to about DP20, or about DP3 to about DP17 or other ranges between about DP3 and about DP30.

In some cases the methods described herein can provide a MIMO composition that has bimodal distribution of two populations of MIMO oligosaccharides, a shorter MIMO population with a DP range from about DP3 to about DP7, and a longer MIMO population with a DP range from about DP9 to about DP25. In some cases, therefore there can be two bell curves or peaks of DP distributions, with a 'valley' of lower DP MIMOs between the two DP peaks.

Definitions

As utilized in accordance with the present disclosure, the following terms, unless otherwise indicated, shall be understood to have the following meanings:

"Brix", also known as degrees Brix (symbol °Bx), refers to the sugar content of an aqueous solution. One degree Brix ($^{\circ}bx$) is 1 gram of sucrose in 100 grams of solution and represents the concentration of the solution as percentage by weight (% w/w). Brix also accounts for dissolved salts, organic acids, and other solutes that increase the refractive index of the solution. As such, it is less useful as a quantitative measure of saccharide content in complex broth (fermentation mixtures), but is quite accurate with respect to the refined product. Thus, 1 degree brix=1 g refractive dry solids per 100 g of material. If the solution contains dissolved solids other than pure sucrose, then the °Bx only approximates the dissolved solid content. However, when the constituent components of the compositions to be compared are similar and/or within similar ranges. Brix values are reproducible and provide an approximation which, in this case, is an accurate (relative to true dry solids via evaporation) measurement of relative dry solids per each composition. Percentages recited herein are %/brix, or % of refractive dry solids, unless otherwise defined.

"Molecular weight distribution," or "MWD" refers to the mass-average molecular weight of a distribution of oligosaccharides.

"Oligosaccharides" refers to glycans of all kinds, generally with a degree of polymerization (DP) greater than or equal to 3 and less than or equal to 18.

"Optical density" or "OD" refers to an estimation of cellular density in a fermentation. Typically used to determine the progress of a fermentation, it is determined via absorbance of light at 600 nm and may be referenced to dry cell mass.

"DE" refers to "dextrose equivalents," and is sometimes used to define the mass average molecular weight distribution (MWD) of starch, maltodextrin, or syrups thereof, created via saccharification of starch with acid and/or enzymes, in terms of the glucose released if fully hydrolyzed. It is also frequently used to describe the glucose equivalent of a maltodextrin mixture, on average, and is an indicator of average molecular weight/DP. It is determined by measurement or reducing power. e.g. a DE=10 maltodextrin mixture would have $\frac{1}{10}^{th}$ the reducing power of an equivalent amount of glucose (or other constituent reducing sugar).

DP refers to the degree of polymerization. The degree of polymerization, or DP, is usually defined as the number of monomeric units in a macromolecule or polymer or oligomer molecule. Hence the "DP", as used herein refers to the number of sugar units in a given oligosaccharide.

"HPAEC-PAD" refers to a hyphenated instrumental analytical technique known as High Pressure Anion Exchange (HPAEC) liquid chromatography (ThermoDionex ICS-5000+) with a Pulsed Amperometric Detector (PAD). Under the scope of this work, this instrument is used solely for the high-resolution separation (ThermoDionex Carbopac PA-100, pH >12.5, acetate gradient elution) of sugar alcohols, mono and disaccharides, and oligosaccharides. Quantification is done via internal standard using L-arabinose and response factors relative to either the pure compound or to a purified maltodextrin of equivalent molecular weight.

"HPLC-RID" refers to a hyphenated instrumental analytical technique known as High Pressure Liquid Chromatography (HPLC, Agilent 1100) with a Refractive Index Detector (RID). Under the scope of this work, this instrument is used to separate (BioRad Aminex HPX-87H, 0.008N $H_2SO_4$ isocratic) and quantify organic (carboxylic) acids that result from bacterial fermentation. This instrument is also used to confirm DP 3, maltose, and mannitol. Quantification is done via external standard method vs. a mixed standard made from target compounds of known purity.

Mineral additives and nutrients can be reagent-grade and can be from the same sources given here:

| | kg: | Mfg: | Cat. #: | Lot #: |
|---|---|---|---|---|
| Water | 1.500 | House DI | n/a | n/a |
| $MnSO_4$—$H_2O$ | 0.00002 | J. T. Baker | 2550-01 | 0000073473 |
| $MgSO_4$ | 0.00025 | Amresco | E797 | 1043C119 |
| $FeSO_4$—$7H_2O$ | 0.00002 | Amresco | 0387 | 1273C446 |
| $KH_2PO_4$ | 0.00555 | Alfa Aesar | 11594 | D05Z029 |
| NaCl | 0.00002 | BDH | BDH9286 | 3424C512 |
| $CaCl_2$ | 0.00012 | Alfa Aesar | 33296 | N11A009 |
| Yeast extract | 0.01044 | Marcor | Bact. Grade | M-14076-1 |

Starch refers to amylose/amylopectin derived from one or more plants. One example, of a starch that can be employed is potato starch (e.g., Sigma-Aldrich #S4251, lot #BCBQ4413V). Other sources of vegetable starch, including those derived from wheat, corn, tapioca, cassava. etc. can also be employed. In some cases, the starch that is employed yields an appropriate DE (e.g., DE 15-100) and brix using α-amylase and/or β-amylase, isoamylase, or any mixture thereof.

Amylase refers to a host of enzymes which, commercially, are typically produced from either bacteria or fungi. These enzymes catalyze the hydrolysis of specific carbohydrate linkages, α-(1,4) in this case, to break down starch into smaller molecules that can be consumed metabolically. There are several types of amylase enzymes including α-(1,4-α-D-glucan glucanohydrolase), β-(1,4-α-D-glucan maltohydrolase), and γ-(1,4-α-D-glucan glucohydrolase) amylases. Because the α-type acts on random locations on the starch molecules, the kinetics of liquefaction are much faster than those observed in the β-type, which releases maltose molecules one at a time beginning with the non-reducing end. While the β-type is more efficient in the production of maltose, mixtures of gelatinized starch at concentrations sufficient to yield the target brix are intractable (in terms of viscosity and gelation). γ-type amylases, also known as glucoamylases, can also cleave α-(1,6) linkages, and will also yield glucose from maltose. Because our product contains α-(1,6) linkages and our target molecule is maltose, residual activities of this amylase type should be rigorously avoided while selecting an enzyme to use in this process. Depending on the organism from which the enzyme is sourced, there can be a significant difference in terms of optimal pH and thermal stability.

Termamyl® refers to α-amylase derived from *Bacillus lichenformis*. It is an α-amylase that is particularly stable at high temperatures (a significant fraction of an added dose is still amylolytic at 100° C.). Because the gelation temperature of starch tends to be within 75-90° C., depending on the source, and enzymes have temperature-dependent turn-over rates, starch can be gelatinized and converted to maltose simultaneously allowing for concentrated solutions to be prepared. The source of this enzyme, Sigma A3403 lot #SLBK3081V, was demonstrated to be free of glucoamylase-activity. Any thermostable amylase of this type may be suitable for use in the process of the producing the composition described herein.

"De-branching enzyme" or "isoamylase" refer to a class of enzymes, similar to amylase, but with specificity for α-(1,6) glucosidic linkages. Examples include dextranase, pullalanase, etc. Maltose yields from starch can be significantly improved via use of these enzymes because de-branching amylopectin renders the polyglucan available, sterically, to α-amylase.

Saccharification refers to the process whereby vegetable starches (or other α-(1,4) linked polyglucans) are hydrolyzed via acidic catalysis or with enzymes, into smaller, soluble components. In this case, maltose is the most desired product, so an α-amylase enzyme, free of glucoamylase-activity is preferred.

Saccharificate refers to the product of a saccharification process.

Maltodextrin refers to a mixture of α-(1,4) linked glucooligosaccharides (linear and branched or "limit dextrins") in saccharificate of starch. DE typically ranges from 13-17. In the work described herein, the term is also used to describe the linear oligosaccharides between DP 3-30, which are used for purposes of instrument calibration and are typically found in our products made using high-maltose syrup and/or starch.

Sucrose refers to α-D-glucopyranosyl-(1→2)-β-D-fructofuranoside, two grades: first, food-grade Refined white sugar from cane (Market Pantry lot #45114A) and, second, a commercial grade raw sugar (not suitable for direct human consumption) obtained from Lula Sugar Factory, 351 Hwy. 999 Belle Rose, La. 70544. All refined white sugars from cane are equivalent for the purposes stated herein. All very high purity (VHP) commercial raw sugars from cane are equivalent for the purposes stated herein. Lesser grades of raw sugar may be used, including molasses. However it is advisable to analyze such lesser grade sources of raw sugar prior to use, for example, to identify its composition and/or to evaluate its performance in a small batch fermentation. Knowledge of the composition of the raw sugar clarifies how much of the raw sugar to use relative to the non-food-grade maltose so that the ratio of sucrose:maltose remains within an acceptable range.

Satin Sweet™ refers to a high-maltose syrup produced by Cargill (lot #E154766, 17540 Monroe Wapello Rd. Eddyville, Iowa. 52553) with a declared certification of analysis (COA) specifying 80.5% dry solids, pH 3.99, fructose, 0.0%; dextrose, 2.8%; maltose, 66.4%; triose, 20.6% and 10.2% higher sugars. In-house verification via HPAEC-PAD defined the composition of the lot as:

| | |
|---|---|
| Brix g/100 g DS | 82.7 |
| glucose, %/brix | 2.21 |

-continued

| | |
|---|---|
| maltose, %/brix | 65.70 |
| DP 3, %/brix | 16.24 |
| DP 4, %/brix | 2.29 |
| DP 5, %/brix | 0.76 |
| DP 6, %/brix | 0.39 |
| DP 7, %/brix | 0.09 |

Other high-maltose syrups meeting these specifications, e.g. Hi Maltose 65 (Batory Foods, 1881 Touhy Ave. Elk Grove, Ill. 60007) are likewise suitable.

The Examples illustrate some of the experimental work performed in the development of the invention.

Example 1: Generating Maltosyl-Isomaltooligosaccharides (MIMOs) Using Satin Sweet™ as a Source of Maltose Satin Sweet™ is a high-maltose syrup prepared from corn starch. It is less expensive than high purity (e.g. >93%) maltose. This Example illustrates that Satin Sweet™ is an appropriate substitute for high purity maltose when making MIMOs for animal feed, providing a MIMO product with a distribution of MIMO oligosaccharides that, with the exception of maltodextrins DP 3-5, was similar to food-grade ISOThrive™ product with respect to MWD for MIMO.

Methods

The feedstock purity of Satin Sweet™ was measured via HPLC. Satin Sweet™ was diluted and analyzed for glucose, maltose and higher oligomers via High-Pressure Anion Exchange chromatography (HPAEC, ThermoDionex ICS-5000+) via Carbopac PA-100 column eluted with a sodium acetate gradient at constant pH (<12.7 NaOH) and pulsed amperometric detection (PAD). The components were quantitated via internal standard method using L-arabinose.

The determined purity was used to calculate the amount of Satin Sweet™ required to have a sucrose:maltose ratio (S/M, w/w) of 2.75 at the time of inoculation. The sucrose:maltose ratio of the starting media was confirmed via HPLC-RID using a BioRad Aminex HPX-87P column standardized with the pure compounds (Sigma Aldrich).

Fermentation procedures similar to those described in U.S. Provisional Application 62/280,026 (which is incorporated herein by reference in its entirety), except for the use of Satin Sweet™ as a source of maltose.

The fermentation medium components listed in the table below were added to a two liter bio-reactor (Eppendorf Celligen 115).

| Fermentation Components | | |
|---|---|---|
| | kg: | g: |
| water: | 1.818 | |
| sucrose | 0.280 | |
| MnSO$_4$•H$_2$O | 0.00002 | 0.02093 |
| MgSO$_4$ | 0.00020 | 0.20312 |
| FeSO$_4$•7H$_2$O | 0.00002 | 0.02160 |
| KH$_2$PO4 | 0.00557 | 5.56501 |
| NaCl | 0.00002 | 0.02068 |
| CaCl$_2$•2H$_2$O | 0.00011 | 0.11113 |
| Yeast | 0.01043 | 10.42705 |
| total kg: | 2.114 | |
| total, L: | 1.971 | |

The contents of the fermenter were adjusted to pH 7.00 using NaOH (50%$_{(aq)}$). The liquor was sampled (pre-autoclave sample). The pH probe was re-calibrated, the fermenter sealed, and the whole was autoclaved at 121° C. for 15 minutes. The liquor was sampled again (sterile needle, post-autoclave sample). The samples were analyzed by HPLC [BioRad Aminex HPX-87P, eluted with water, isocratic. Agilent 1100 HPLC with refractive index detector (RID)] via external standard method to detect possible inversion of sucrose. Significant inversion of the sucrose was not observed, but the brix increased by 0.9%:

| Sample | Comp.: | % w/w: | brix meas: | %/brix: | Suc, %: |
|---|---|---|---|---|---|
| Pre-Autoclave | sucrose | 12.400 | 13.3 | 93.25 | |
| | maltose | 0.000 | | 0.00 | |
| Post-Autoclave | sucrose | 13.227 | 14.2 | 93.15 | −0.10 |
| | maltose | 0.00 | | 0.00 | |

Separately, an inoculum medium containing the components listed in the table below was prepared in a 500 mL Erlenmeyer flask using sucrose (99.9% refined white cane sugar) for initial growth of the microorganism used for fermentation (*Leuconostoc citreum* NRRL B-742 (ATCC 13146)). Note that Satin Sweet® was the only source of maltose in the medium shown below, and that by employing 12.22 g Satin Sweet®, the amount of maltose added to the pre-inoculum starter medium was 6.606 g.

| Pre-Inoculum Starter Medium (into autoclave) Amount Satin Sweet ®: 12.22 g | | |
|---|---|---|
| | kg: | g: |
| water: | 0.087557 | 87.5571 |
| sucrose | 0.01220 | 12.2000 |
| Maltose-H$_2$O | 0.006606 | 6.60582 |
| MnSO$_4$•H$_2$O | 1.05E-06 | 0.00105 |
| MgSO$_4$ | 1.02E-05 | 0.01015 |
| FeSO$_4$•7H$_2$O | 1.08E-06 | 0.00108 |
| KH$_2$PO4 | 0.000278 | 0.27811 |
| NaCl | 1.03E-06 | 0.00103 |
| CaCl$_2$•2H$_2$O | 5.55E-06 | 0.00555 |
| Yeast | 0.000521 | 0.52110 |
| total kg: | 0.107 | |
| total, L: | 0.100 | |

The growth of the fermentation organism was started by addition of 0.5 mL of stationary growth-phase flask culture [*Leuconostoc* citreum NRRL B-742 (ATCC 13146) in rich media] and 0.5 mL 40% w/w glycerol$_{(aq)}$ (kept at −75° C.) to the inoculum flask. The flask was then incubated with shaking for 16 hr at 27° C.

The amount of Satin Sweet® required for the bulk fermentation was calculated (to account for any loss of sucrose) to be 0.209 kg. The Satin Sweet® was fluidized in about 50 mL sterile water and the mixture was poured quickly into the bioreactor though a sterilized funnel. The whole was agitated until moiré patterns ceased (indicated complete mixing).

The pre-inoculum medium was sampled and analyzed by HPLC-RID (BioRad Aminex HPX-87P, isocratic water, Agilent 1100 HPLC] via external standard method to determine the starting sucrose:maltose ratio (S/M, w/w). The results are shown in the table below.

| Pre-Inoculum Medium Sucrose and Maltose Content | | | | | |
|---|---|---|---|---|---|
| | Comp.: | % w/w: | brix: | %/brix: | S/M: |
| Pre-inoculum | sucrose | 10.907 | 19.50 | 55.93 | 2.742 |
| | maltose | 3.98 | 19.50 | 20.40 | |

Twenty five (25) mL inoculum was transferred to the 2 L bioreactor via a sterile needle. The pH was measured, the probe zeroed accordingly, and the pH was adjusted to 6.5 using either HCl (37%) or NaOH (50% w/w). pH was set to control at pH 5.5 using NaOH (40% w/w).

The reactor was sampled at 24 hours, 29 hours, and 48 hours. The pH was compared against a bench meter and the probe was zeroed as needed. The samples were centrifuged and filtered (0.2 μm filter), and analyzed for carbohydrates/mannitol via HPAEC-PAD and organic acids using HPLC-RID (BioRad Aminex HPX-87H, isocratic 0.008 mM $H_2SO_4$).

Results

The composition of the resulting fermentation broth, relative to sampling interval, is shown in the table below. The values shown are %/brix (refractive dry solids).

| Composition of Fermentation over Time | | | | |
|---|---|---|---|---|
| Trial: | #1 | #1 | #1 | #1 |
| Hr: | Pre | 24 | 29 | 48 |
| brix: | 19.9 | 20.0 | 20.0 | 19.8 |
| mannitol | 0.00 | 0.80 | 10.26 | 24.08 |
| fructose | 0.01 | 4.12 | 0.56 | 0.08 |
| sucrose | 55.93 | 31.15 | 4.08 | 1.25 |
| maltose | 20.40 | 15.42 | 2.63 | 3.11 |
| MIMO-DP 3 | 0.00 | 10.43 | 12.04 | 8.79 |
| MIMO-DP 4 | 0.00 | 2.20 | 21.87 | 20.14 |
| 1,4-DP3 | 3.42 | 6.60 | 6.61 | 6.80 |
| MIMO-DP 5 | 0.00 | 0.22 | 13.41 | 13.96 |
| MIMO-DP 6 | 0.00 | 0.00 | 4.18 | 5.25 |
| MIMO-DP 7 | 0.00 | 0.00 | 1.63 | 2.14 |
| MIMO-DP 8 | 0.00 | 0.00 | 0.00 | 0.87 |
| 1,4-DP4 | 0.28 | 0.50 | 2.51 | 2.80 |
| MIMO-DP 9 | 0.00 | 0.00 | 0.00 | 0.00 |
| lactate | 0.00 | 0.84 | 4.23 | 10.79 |
| glycerol | 0.00 | 0.06 | 0.05 | 0.13 |
| formate | 0.00 | 0.00 | 0.00 | 0.02 |
| acetate | 0.00 | 0.19 | 1.69 | 4.10 |
| TOTAL: | 80.94 | 73.28 | 91.04 | 104.30 |
| MIMO, %: | 0.00 | 12.85 | 53.13 | 51.14 |
| Purity, %: | 0.00 | 17.53 | 58.36 | 49.03 |
| MWD: | 342.00 | 430.70 | 693.21 | 723.72 |
| Yield %: | 0.00 | 20.22 | 67.30 | 55.98 |

Pre refers to pre-inoculation medium.

Initiation of log-growth took 6 hours post inoculation (FIG. 1). Log-growth correlated with a sharp increase in the mass-average molecular weight distribution (MWD) of MIMOs between 24 and 29 hours, as shown in FIG. 1.

Figure 2:
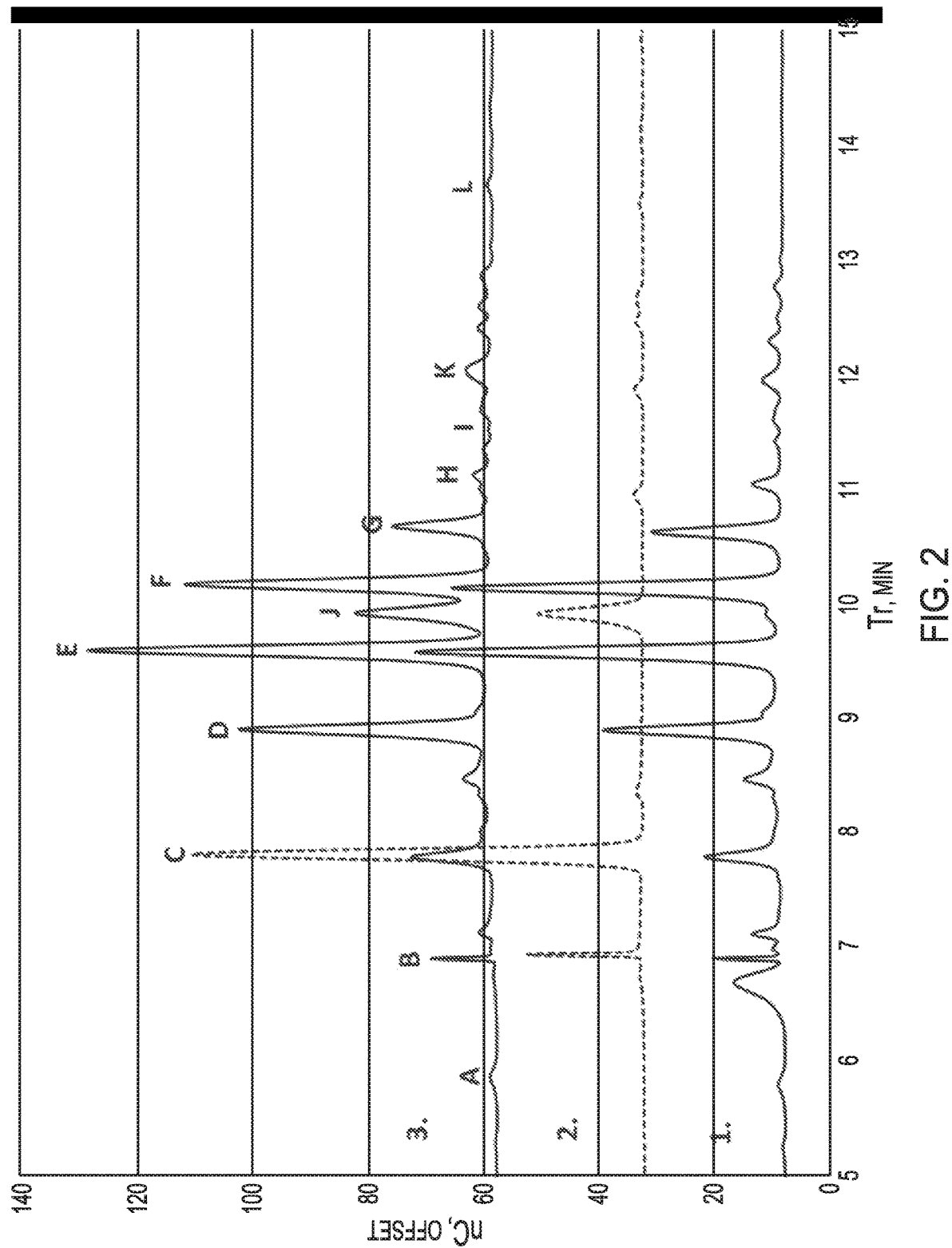
FIG. 2 shows a comparison of HPAEC-PAD chromatograms of the following: 1. Food-grade MIMO broth, 2. Satin Sweet™ scaled down by a factor of 5, and 3. Animal Feed Grade MIMO broth made from Satin Sweet™ High maltose syrup and refined white sugar (sucrose) from cane. Peak A corresponds to D-leucrose, peak B corresponds to sucrose; peak C corresponds to maltose; peaks D-I correspond to MIMO DPs 3-8, and peaks J-L correspond to maltodextrins DP 3-5. With the exception of maltodextrins with DP 3-5, the product conformed, chromatographically, with a food-grade MIMO product suitable for human consumption.

As shown in FIG. 2, the chromatographic profile of the product is similar to the food-grade ISOThrive™ MIMO product. FIG. 2 shows a comparison of HPAEC-PAD chromatograms of:
1. Food-grade MIMO broth,
2. Satin Sweet™ scaled down by a factor of 5, and
3. Animal Feed Grade MIMO broth made from Satin Sweet™ High maltose syrup and refined white sugar (sucrose) from cane.

The peaks shown correspond to: (A) D-leucrose; (B) sucrose; (C) maltose; (D)-(I) MIMO DP 3-8; and (J)-(L) maltodextrins DP 3-5. With the exception of additional maltodextrins DP 3-5, the MIMO product component, with respect to MWD, conformed chromatographically with a food-grade product suitable for human consumption.

Example 2: Generating Maltosyl-Isomaltooligosaccharides (MIMOs) Using Satin Sweet™ as a Source of Maltose and Raw Sugar as a Source of Sucrose In order to recognize further savings in feedstock costs, refined white sugar was replaced with commercial raw sugar. Commercial raw sugars are not human food-grade because they contain various impurities, but are significantly less expensive than food-grade refined white sugar (~$0.09/lb world-market, ~$0.22/lb U.S. market vs 50.42/lb refined white). This Example illustrates that raw sugar is an appropriate substitute for white sugar (and Satin Sweet® for maltose) in the production of a MIMO product suitable for use in animal feed, providing a MIMO product with a distribution of MIMO oligosaccharides that, with the exception of maltodextrins DP 3-5, was similar to food-grade ISOThrive™ product.

Methods

The purity of raw cane sugar grab sample (Lula sugar factory, Louisiana) was measured via HPLC [BioRad Aminex HPX-87P, eluted with water, isocratic Agilent 1100 HPLC with refractive index detector (RID)] via external standard method outlined in U.S. Provisional Application 62/280,026, filed Jan. 18, 2016 by Madsen and Oswald, which is incorporated herein by reference in its entirety. The material contained 98.5% w/w sucrose and had over dry solids, where the remainder is moisture. The purity of the tested sample was not less than 99%.

Fermentation procedures similar to those described in U.S. Provisional Application 62/280,026 (which is incorporated herein by reference in its entirety) were employed, except for the use of Satin Sweet™ as a source of maltose, and raw sugar as a source of sucrose.

The components of the pre-inoculum medium are shown in the table below. The Pre-Inoculum Medium was then sterilized in an autoclave. Note that Satin Sweet® was the only source of maltose in the medium shown below, and that by employing 12.22 g Satin Sweet®, the amount of maltose added to the pre-inoculum starter medium was 6.61 g. Similarly, raw sugar was the only source of sucrose in the pre-inoculum starter medium so while 12.755 g of raw sugar was employed, the amount of sucrose in the pre-inoculum starter medium was 12.56 g.

| Pre-Inoculum Starter Medium (before autoclaving) | | |
|---|---|---|
| Satin sweet ® | 12.220 g | |
| Raw Sugar | 12.755 g | |
| Component | Kg | grams |
| Sucrose | 0.01256 | 12.5566 |
| Maltose $H_2O$ | 0.00676 | 6.75578 |
| $MnSO_4 \cdot H_2O$ | 1.05E-6 | 0.00105 |
| $MgSO_4$ | 1.02E-5 | 0.01015 |
| $FeSO_4 \cdot 7H_2O$ | 1.08E-6 | 0.00108 |
| $KH_2PO_4$ | 0.00028 | 0.27811 |
| NaCl | 1.03E-6 | 0.00103 |
| $CaCl_2 \cdot 2H_2O$ | 5.56E-5 | 0.00555 |
| Yeast | 0.00052 | 0.52594 |
| total kg: | 0.108 | |
| total, L: | 0.100 | |

The growth of the fermentation organism in the pre-inoculum medium was started by addition of 0.5 mL of stationary growth-phase flask culture [*Leuconostoc citreum* NRRL B-742 (ATCC 13146) in rich media] and 0.5 mL 40% w/w glycerol$_{(aq)}$ (kept at −75° C.) to the inoculum flask. The flask was then incubated with shaking for 16 hr at 27° C.

The fermentation medium components listed in the table below were added to a two liter bio-reactor (Eppendorf Celligen 115).

| Fermentation Medium | | |
|---|---|---|
| Component | Kg | grams |
| water: | 1.818 | |
| Raw Sugar | 0.285 | |
| MnSO$_4$•H$_2$O | 0.00002 | 0.02139 |
| MgSO$_4$ | 0.00021 | 0.21062 |
| FeSO$_4$•7H$_2$O | 0.00002 | 0.02261 |
| KH$_2$PO4 | 0.00556 | 5.56124 |
| NaCl | 0.00002 | 0.02144 |
| CaCl$_2$•2H$_2$O | 0.00011 | 0.11086 |
| Yeast | 0.01043 | 10.43362 |
| total kg: | 2.119 | |
| total, L: | 1.981 | |

The contents of the fermentation starter medium were adjusted to pH 7.00 using NaOH (50%$_{(aq)}$) and the liquor was sampled (pre-autoclave sample). The pH probe was re-calibrated, the fermenter scaled, and the contents were allowed to sit with stirring for 1 Hr. The whole mixture was then autoclaved at 121° C. for 30 minutes. The liquor was sampled again (sterile needle, post-autoclave sample). The samples were analyzed by HPLC [BioRad Aminex HPX-87P, eluted with water, isocratic, Agilent 1100 HPLC with refractive index detector (RID)] via external standard method to check for possible inversion of sucrose. As before, very little if any inversion of sucrose took place; the Δ sucrose was only −0.1%.

The amount of Satin Sweet® required for the bulk fermentation was calculated (to account for any loss of sucrose) to be 0.208 kg. The Satin Sweet was fluidized (in about 100 g sterile water) and poured quickly into the bioreactor though a sterilized funnel. The whole mixture was agitated until moiré patterns ceased (indicating complete mixing).

Twenty five (25) mL inoculum was transferred to the 2 L bioreactor via sterile needle. The pH was measured, and the pH was adjusted to 6.5 using either HCl (37%) or NaOH (50% w/w).

The post-inoculum mixture was sampled and analyzed by HPLC-RID (BioRad Aminex HPX-87P, isocratic water, Agilent 1100 HPLC) via external standard method to determine the starting sucrose:maltose ratio (S/M), which is shown in the table below.

| | Component | % w/w: | brix meas: | %/brix: | S/M: |
|---|---|---|---|---|---|
| Post-inoculum | sucrose | 11.774 | 19.5 | 60.38 | 2.69 |
| | maltose | 4.38 | | 21.44 | |

Results

The reactor contents were sampled once the fermentation was complete. The sample was centrifuged, filtered (0.2 μm), and analyzed for carbohydrates/mannitol via HPAEC-PAD and organic acids via HPLC-RID (BioRad Aminex HPX-87H, isocratic 0.008 mM H$_2$SO$_4$).

The composition of the resulting final broth (final) compared to the pre-inoculum media (Pre) is shown in the table below. The values shown are %/brix (refractive dry solids).

| Variable | Pre | Final |
|---|---|---|
| brix: | 19.5 | 18.7 |
| mannitol | 0.00 | 22.49 |
| fructose | 0.00 | 0.02 |
| sucrose | 60.38 | 1.03 |
| maltose | 22.44 | 2.99 |
| MIMO-DP 3 | 0.00 | 6.88 |
| MIMO-DP 4 | 0.00 | 14.07 |
| 1,4-DP3 | 1.69 | 6.29 |
| MIMO-DP 5 | 0.00 | 12.18 |
| MIMO-DP 6 | 0.00 | 5.90 |
| MIMO-DP 7 | 0.00 | 2.33 |
| MIMO-DP 8 | 0.00 | 1.04 |
| 1,4-DP4 | 0.24 | 5.02 |
| MIMO-DP 9 | 0.00 | 0.00 |
| lactate | 0.00 | 16.03 |
| glycerol | 0.00 | 0.35 |
| formate | 0.00 | 0.00 |
| acetate | 0.00 | 4.39 |
| TOTAL: | 85.78 | 101.52 |
| MIMO, %: | 0.00 | 42.40 |
| Purity, %: | 0.00 | 41.77 |
| MWD: | 342.00 | 745.47 |
| Yield %: | 0.00 | 45.76 |

Figure 3:
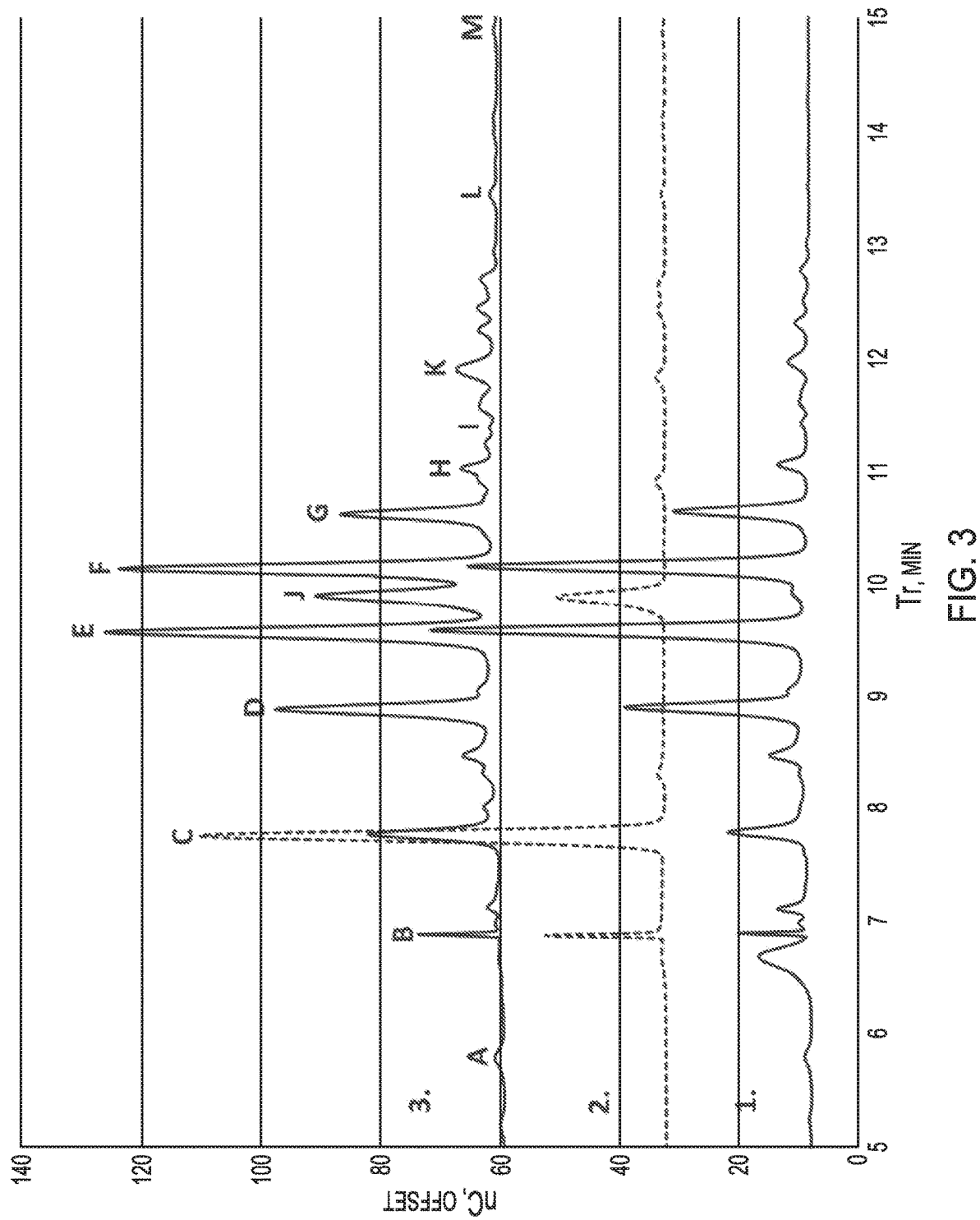
FIG. 3 shows a comparison of HPAEC-PAD chromatograms of the following: 1. Food-grade MIMO broth, 2. Satin Sweet™ scaled down by a factor of 5, and 3. Animal Feed Grade MIMO broth made from Satin Sweet™ High maltose syrup and commercial-grade raw sugar (sucrose) from cane. Peak A corresponds to D-leucrose; peak B corresponds to sucrose; peak C corresponds to maltose; peaks D-I correspond to MIMO DPs 3-8; and peaks J-M correspond to maltodextrins with DP 3-6. With the exception of maltodextrins DP 3-6, the product conformed, chromatographically, with a food-grade product suitable for human consumption.

As shown in FIG. 3, the chromatographic profile of the product is similar to the food-grade ISOThrive™ MIMO product. FIG. 3 shows a comparison of HPAEC-PAD chromatograms of the following:
 1. Food-grade MIMO broth;
 2. Satin Sweet™ scaled down by a factor of 5; and
 3. Animal Feed Grade MIMO broth made from Satin Sweet™ high maltose syrup and commercial-grade raw sugar (sucrose) from sugar cane as described in this Example.

The peaks shown in FIG. 3 are labeled with letters corresponding to the following sugars and oligosaccharides: (A) D-leucrose; (B) sucrose; (C) maltose; (D)-(I) MIMO DP 3-8, and (J)-(M) maltodextrins DP 3-6. With the exception of maltodextrins DP 3-6, the product conformed, chromatographically, with a food-grade product suitable for human consumption.

Example 3: Generating Maltosyl-Isomaltooligosaccharides (MIMOs) Using Potato Starch as a Source of Maltose and Raw Sugar as a Source of Sucrose This Example illustrates that potato starch is a good and inexpensive source of maltose for the preparation of MIMOs.

Preparation of Saccharified Potato Starch

Potato starch (Sigma Aldrich #S4251, lot #BCBJ6787V) was slurry-fed (50-56% w/w in water) into 2 L of 18 MΩ water at 83° C. with pH 5.5, containing 1000 U thermostable α-amylase (Termamyl, *B. lichenformis*, type XII-A, Sigma #A3403, lot #SLBK3081V). The addition of further starch and enzyme aliquots was repeated until the brix (g refractive dry solids/100 g material) determined via refractive index was 26.8 and the purity was sufficient to provide 0.091 kg maltose (as detected by HPLC-RID, Aminex HPX-87H).

The resulting liquor was filtered (Whatman #3 filter paper a with Celite 545 diatomite filter aid pre-coat), and concentrated to 51.85 brix via evaporation (70° C., 26" Hg).

Preparation of Oligosaccharides

Batch fermentation were conducted in a 2 L BioFlow®/CelliGen® 115 fermenter (New Brunswick Scientific Co.). The media pH was adjusted to 7.00 with 50% w/w NaOH (aq). The fermenter was then sealed and the whole mixture autoclaved at 121° C. for 15 minutes. Once cooled, 0.829 kg of maltose syrup derived from potato starch (51.85% brix, 21.1% maltose, sucrose:maltose ratio=2.758) was transferred into the fermenter to give a final media composition of:
  sucrose (9.63%),
  maltose syrup (3.49%),
  $MnSO_4.H_2O$ (0.0008%),
  $MgSO_4$ (0.0096%),
  $FeSO_4.7H_2O$ (0.0008%),
  $KH_2PO_4$ (0.2138%),
  NaCl (0.0008%),
  $CaCl_2.2H_2O$ (0.0046%), and
  yeast extract (0.4022%).

The media pH was adjusted to 6.5 with 37% HCl and then inoculated with 50 ml of late log phase *L. citreum* (ATCC 13146). Fermentation was allowed to proceed with addition of alkali as needed to maintain the pH at 5.5 until fermentation was complete. Samples of pre-inoculation media, 48 hr fermentation liquor, and final fermentation broth were centrifuged at 10 kRPM for 10 minutes and the supernatant filtered through a 0.2 μm nylon syringe filter prior to analysis via HPLC-RID and HPAEC-PAD.

Analysis of Oligosaccharides

Figure 4:
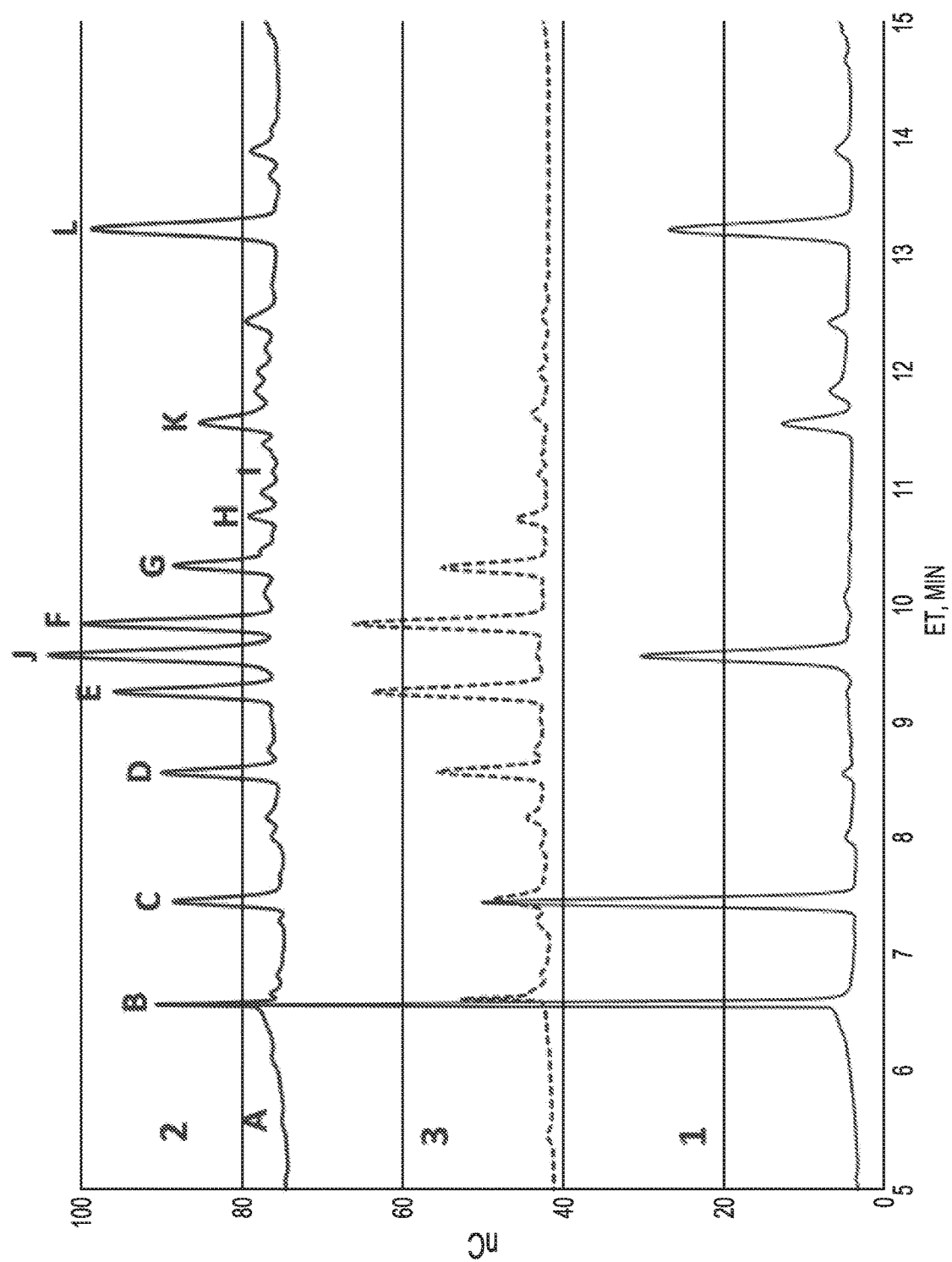
FIG. 4 shows two chromatograms, bottom and top, of the following: 1, pre-inoculum media of sucrose and sacchari- fied potato starch, and 2, final fermentation broth. For comparison, chromatogram 3 is a food-grade decolorized broth made as described by Madsen and Oswald (PCT/US2017/013957 filed Jan. 18, 2017 and U.S. Provisional Application 62/280,026, filed Jan. 18, 2016). Peak A corresponds to D-leucrose; peak B corresponds to sucrose; peak C corresponds to maltose; peaks D-I correspond to MIMO DPs 3-8; and peaks J-L correspond to maltodextrins with DP 3-5. With the exception of maltodextrins DP 3-5, the product conformed, chromatographically, with a food-grade MIMO product suitable for human consumption.

Analysis of the final fermentation media showed that the distribution of oligosaccharides was very similar to the human food-grade MIMO generated as described in U.S. Provisional Application 62/280,026 (which is incorporated herein by reference in its entirety). The mass average molecular weight of the animal feed grade MIMO (Feed GR) was 790.16 Da, while the human food-grade MIMO (Food GR) control was 789.46 Da. This conclusion is visually apparent in FIG. 4, where it can be seen that overlaying the normalized Food Grade MIMO (15-01A) chromatogram onto the Feed Grade (Final) chromatogram shows that the Final Feed Grade product has a similar profile compared to the Food Grade MIMO product.

The final broth so obtained contained the components shown in the following table, where a commercial food-grade (for human consumption) product, 15-01A, is shown for comparison. The values shown are %/brix (refractive dry solids).

| %/brix | 48 Hr | Final | 15-01A |
|---|---|---|---|
| Brix | 25.5 | 26.2 | 25.06 |
| mannitol | 18.28 | 17.35 | 2.51 |
| glucose | 0.44 | 0.93 | 0.34 |
| fructose | 0.00 | 0.00 | 0.05 |
| sucrose | 2.93 | 2.84 | 0.53 |
| maltose | 1.95 | 2.72 | 1.73 |
| panose | 4.65 | 4.43 | 4.69 |
| MIMO-DP4 | 11.33 | 9.96 | 10.36 |
| 1,4-DP3 | 10.66 | 10.23 | 0.00 |
| MIMO-DP5 | 10.29 | 9.05 | 10.44 |
| MIMO-DP6 | 7.08 | 6.82 | 6.15 |
| MIMO-DP7 | 2.94 | 3.12 | 2.16 |
| MIMO-DP8 | 1.85 | 1.69 | 0.93 |
| 1,4-DP4 | 9.93 | 6.33 | 0.00 |
| MIMO-DP9 | 0.00 | 0.00 | 0.23 |
| MIMO-DP10 | 0.00 | 0.00 | 0.00 |
| lactic acid | 8.30 | 8.08 | 0.00 |
| glycerol | 0.24 | 0.23 | 0.17 |
| formic acid | 0.06 | 0.05 | 0.00 |
| acetic acid | 2.92 | 2.86 | 0.00 |
| MIMO | 38.15 | 35.07 | 34.96 |
| MO | 20.59 | 16.56 | 0.00 |
| Total | 93.86 | 86.70 | 40.28 |
| Purity | 40.64 | 40.45 | 86.81 |
| MWD | 795.82 | 790.16 | 789.46 |
| S/M | n/a | n/a | n/a |

Example 4: *Weissella confusa* Production of MIMOs

This Example illustrates that *Weissella confusa* can also be employed as a dextransucrase-producing microorganism useful for making MIMOs.

Methods

To a 20 L fermenter was added deionized water 10.022 kg, sucrose 1.963 kg, yeast extract 75.0000 g, $MnSO_4$ 0.15045 g, $MgSO_4$ 1.47794 g. $FeSO_4$ 0.15564 g. $KH_2PO_4$ 40.11177 g, NaCl 0.15521 g, and $CaCl_2$) 0.63645 g. The pH was adjusted to 5.62 using NaOH (50%), 15.99257 g. The whole was sterilized in place and 0.790 kg of maltose monohydrate is dissolved into 2.000 kg freshly autoclaved deionized water. The latter was transferred to the fermenter via 0.2 micron membrane. The whole was inoculated with 150 mL of a late-log culture of *Weissella confusa* NRRL B-1064 in MRS media. During incubation, the temperature was maintained at 27-30° C., and the pH controlled at 5.00 using NaOH (40%). The fermentation was allowed to proceed for 60 Hr. The resulting broth was centrifuged to remove the cells (9000 RPM/20 min.) and analyzed via HPAEC-PAD and HPLC-DRI.

Results

The composition of the final fermentation broth is shown below. The values shown are %/brix (refractive dry solids).

| Component | %/brix |
|---|---|
| brix | 16.00 |
| mannitol | 0.07 |
| glucose | 0.44 |
| fructose | 9.79 |
| leucrose | 3.01 |
| sucrose | 0.98 |
| maltose | 0.84 |
| MIMO-DP3 | 2.72 |
| MIMO-DP4 | 4.50 |
| MIMO-DP5 | 4.51 |
| MIMO-DP6 | 4.46 |
| MIMO-DP7 | 3.83 |
| MIMO-DP8 | 4.02 |
| MIMO-DP9 | 3.34 |
| MIMO-DP10 | 4.93 |
| MIMO-DP11 | 3.39 |
| MIMO-DP12 | 2.98 |
| MIMO-DP13 | 2.93 |
| MIMO-DP14 | 2.55 |
| MIMO-DP15 | 2.18 |
| MIMO-DP16 | 1.37 |
| MIMO-DP17 | 1.06 |
| MIMO-DP18 | 1.38 |
| MIMO-DP19 | 1.17 |
| MIMO-DP20 | 0.64 |
| MIMO-DP21 | 0.67 |
| MIMO-DP22 | 0.79 |
| MIMO-DP23 | 0.66 |
| lactic acid | 20.58 |
| glycerol | 1.04 |

-continued

| Component | %/brix |
|---|---|
| formic acid | 0.00 |
| acetic acid | 1.04 |
| ethanol | 8.15 |
| MIMO, tot: | 54.06 |
| Total: | 100.00 |
| Purity, %: | 54.06 |
| MWD, Da: | 1619.2 |

Figure 5:
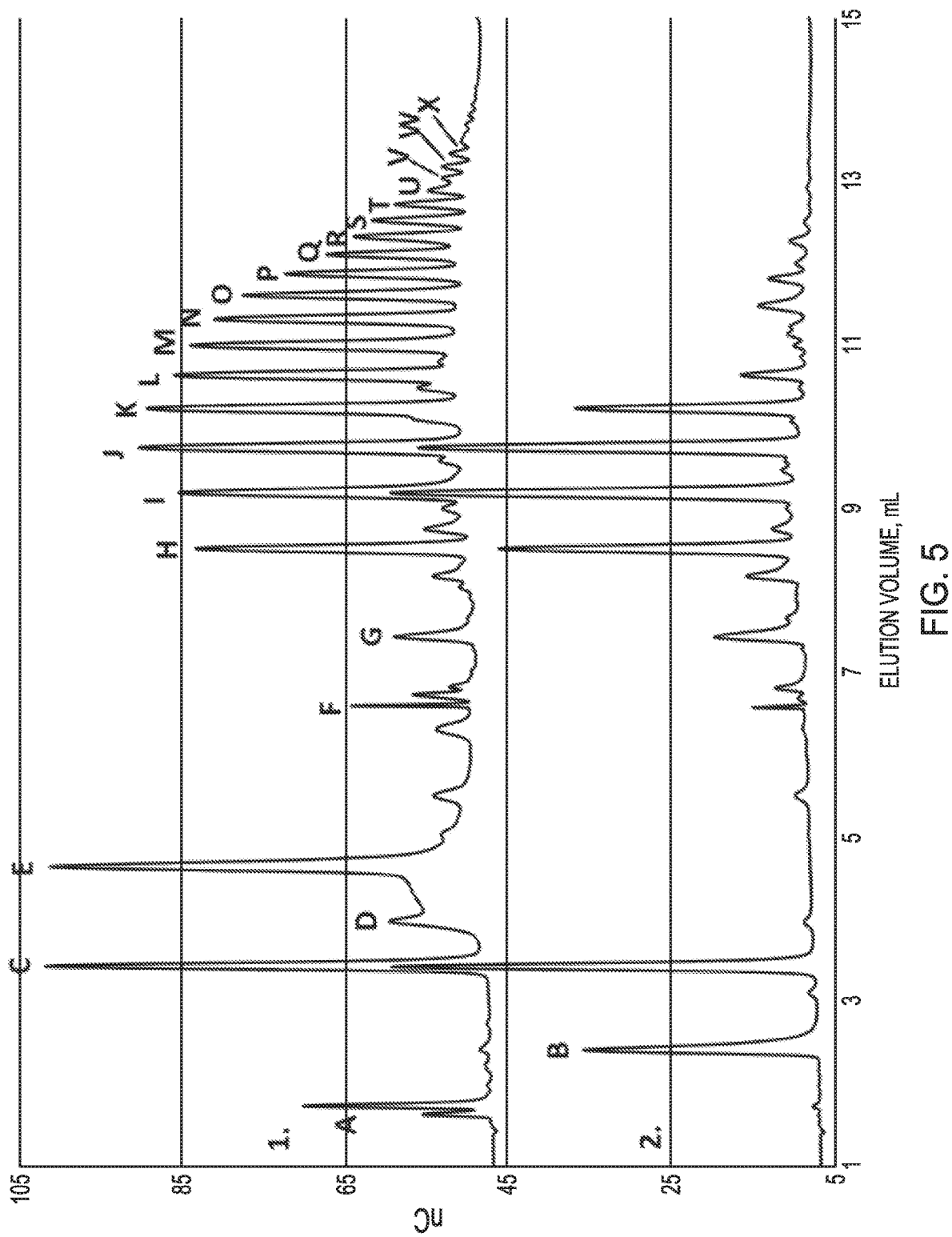
FIG. 5 shows two HPAEC chromatograms, where the top chromatogram (designated 1) illustrates the composition of media broth from a culture of *W. confusa* NRRL B-1064, and the bottom chromatogram (designated 2) illustrates a product made via fermentation with *L. citreum* NRRL B-742. Peak A corresponds to glycerol, peak B corresponds to mannitol, peak C corresponds to L-arabinose (IS), peak D corresponds to glucose, peak E corresponds to fructose, peak F corresponds to sucrose, peak G corresponds to maltose, and peaks H-X correspond to MIMOs with DP values of DP3 to D19.

FIG. 5 illustrates the composition of the *Weissella confusa* fermentation broth as detected by HPAEC analysis, demonstrating that *Weissella confusa* is a dextransucrase-producing microorganism useful for making MIMOs.

REFERENCES

1. Swartz, M. N. (2002) *Human Diseases Caused by Foodborne Pathogens of Animal Origin. Human Disease and Foodbourne Pathogens.* Clin. Infect. Dis. 2002:34 pp. S111-S122 (see website at cid.oxfordjournals.org/content/34/Supplement_3/S111.full.pdf+html).
2. Bergeron, C. R., Prussing, C., Boerlin, P., Daignault, D., Dutil, L., Reid-Smith, R. J., Zhanel, G. G, and Manges, A. R. (2012) *Chickens as Reservoir for Extraintestinal Pathogenic Escherichia coli in Humans, Canada.* Emerging Infectious Diseases 18 (3), pp. 415-421 (see website at CDC.gov/eid).
3. Evangelisti, D. G., English, A. R., Girard, A. E., Lynch, J. E, and Solomons, I. A. (1975) *Influence of Subtherapeutic Levels of Oxytetracycline on Salmonella typhimurium in Swine, Calves, and chickens*, Antimicrob. Agents Chemother. 8(6), pp. 664-672 (see website at www.ncbi.nlm.nih.gov/pmc/articles/PMC429444/).
4. Phillips, I., Casewell. M., Cox. T., De Groot. B., Friis, C., Jones. R., Nightingale, C., Preston, R, and Waddell, J. (2004) *Does the use of antibiotics in food animals pose a risk to human health? A critical review of the published data.* J. Antimicrob. Chemother. 53. pp. 28-52 (see website at jac.oxfordjournals.org/content/53/1/28.full.pdf+html).
5. National Research Coucil (US) Committee to Study the Human Health Effects of Subtherapeutic Antibiotic use in Animal Feeds. Washington (DC). (1980). *The Effects on Human Health of Subthempeutic Use of Antimicrobials in Animal Feeds.* Appendix K Antibiotics in Animal Feeds. (see website at www.ncbi.nlm.nih.gov/books/NBK216502/).
6. Hu, Y., Ketabi. A., Buchko. A, and Ganzle. (2013) *Metabolism of Isomalto-oligosaccharides by Lactobacillus reuteri and bifidobacteria.* Lett. Appl. Microbiol. 57, pp. 108-114.
7. Bounaix M-S., Robert H., Gabriel V., Morel S., Remaud-Simeon M., Gabriel B. and Fontagne-Faucher C. (2010). *Characterization of dextran-producing Weissella strains isolated from sourdoughs and evidence of constitutive dextransucrase expression.* FEMS Microbiol Lett 311 (1), pp. 18-26. DOI: 10.1111/j.1574-6968.2010.02067.x.
8. Shi Q., Hou Y, Juvonen M, Tuomainen P, Kajala I, Shulka S, Goyal A, Maaheimo H, Katina K, and Tenkanen M. (2016). *Optimization of isomaltooligosaccharide size distribution by acceptor reaction of Weissella confusa Dextransucrase and characterization of novel α-(1→2)-brunched isomaltooligosaccharides.* J Agric Food Chem 64, pp. 3276-3286. Doi: 10.1021/acs.jafc.6b01356.
9. Torino M I., Font de Valdez G, and Mozzi F. (2015). *Biopolymers from lactic acid bacteria. Novel applications in foods and beverages.* Front Microbiol. 6 (834) pp. 1-16. doi: 10.3389/fmicb.2015.00834

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements summarize some of the features of the invention.

Statements:

1. A method comprising contacting a dextransucrase-producing microorganism with an aqueous culture medium comprising a ratio of sucrose to maltose ranging from about 0.2 to about 7.0 to form a fermentation mixture, where at least one source of the sucrose and the maltose is an impure source of sucrose or maltose, to thereby generate a composition comprising maltosyl-isomaltooligosaccharide with a mass average molecular weight distribution of about 650 to 2000 daltons.
2. The method of statement 1, where the dextransucrase-producing microorganism is *Leuconostoc mesenteroides, Leuconostoc citreum, Leuconostoc gasicomitatum, Leuconostoc kimchi, Leuconostoc amelibiosum, Weissella confusa, Weissella cibaria, Lactococcus* spp., *Streptococcus mutans*), *Lactobacillis* spp. (e.g., *Lactobacillis reuteri, Lactobacillis hilgardii, Lactobacillis acidophilus, Lactobacillis plantarum, Lactobacillis fermentum, Lactobacillis sakei*), *Pediococcus pentosaceus* spp. (e.g., *Pediococcus pentosaceus* (ATCC #33316), *Pediococcus acidilactici*), or a mixture thereof.
3. The method of statement 1 or 2, where the dextransucrase-producing microorganism is *Leuconostoc mesenteroides* ATCC 13146, *Weissella confusa, Weissella cibaria, Leuconostoc mesenteroides* NRRL B-742, *Leuconostoc mesentemides* subsp. *mesenteroides* (Tsenkovskii) van Tieghem (ATCC®11449™), or *Leuconostoc citreum* NRRL B-1299].
4. The method of any of statements 1-3, where the dextransucrase-producing microorganism is *Leuconostoc citreum* ATCC 13146 (NRRL B-742), *Weissella confusa*, or a combination thereof.
5. The method of any of statements 1-4, where the impure source of sucrose or maltose does not contain toxic compounds, heavy metals, or toxic materials detectable by HPAEC-PAD, HPLC, ICP-MS, or HPLC-RID.
6. The method of any of statements 1-5, where the impure source of sucrose or maltose contains less than 100% sucrose or maltose, or less than 99%, or less than 99.5%, or less than 98%, or less than 98.5%, or less than 98%, or less than 97%, or less than 96%, or less than 95%, or less than 90%, or less than 85%, or less than 80%, or less than 75%, or less than 70%, or less than 67%, or less than 66%, or less than 65% sucrose or maltose.
7. The method of any of statements 1-6, where the impure source of sucrose or maltose is a non-food-grade source of sucrose or maltose.

8. The method of any of statements 1-7, where the sucrose is, or is derived from, commercial raw sugar from cane, molasses, syrup from sugarcane, sweet sorghum, energy cane, beet sugar, maple syrup, or any combinations thereof.

9. The method of any of statements 1-8, where the maltose is, or is derived from, maltose syrup, high maltose syrup, malt, saccharified starch, corn/maize starch, potato starch, tapioca starch, wheat starch, oat starch, millet/sorghum starch, rice starch, arrowroot starch, taro starch, kudzu starch, yam starch, and/or any combination thereof.

10. The method of any of statements 1-9, where the maltose is, or is derived from, a high-maltose syrup.

11. The method of any of statements 1-10, where the sucrose:maltose ratio is from 2.0 to about 4.5 when contacting the dextransucrase-producing microorganism with the aqueous culture medium.

12. The method of any of statements 1-11, where the sucrose:maltose ratio ranges from about 0.20 to about 7.0, or from about 2.0 to about 4.5, or from about 2 from about 2.2 to about 4.3, or about 2.3 to about 4.0, or about 2.4 to about 4.0, or about 2.5 to about 3.75, or about 2.5 to about 3.5, or about 2.5 to about 3.0, or from about 0.3 to about 6.0, or from about 0.5 to about 5.0, or from about 2.0 to about 4.5, or from about 2 from about 2.2 to about 4.3, or about 2.3 to about 4.0, or about 2.4 to about 4.0, or about 2.5 to about 3.75, or about 2.5 to about 3.5, or about 2.5 to about 3.0, or about 2.75.

13. The method of any of statements 1-12, where the sucrose:maltose ratio about 2.75.

14. The method of any of statements 1-13, where the aqueous culture medium comprises minerals, and nutrients for the dextransucrase-producing microorganism.

15. The method of any of statements 1-14, where the aqueous culture medium is a media that can facilitate fermentation.

16. The method of any of statements 1-15, where the aqueous culture medium comprises corn steep liquor and/or solids.

17. The method of any of statements 1-16, where the aqueous culture medium comprises a manganese salt, a magnesium salt, an iron salt, a potassium salt, a sodium salt, a calcium salt, and yeast extract.

18. The method of any of statements 1-17, where the fermentation mixture comprises the non-food-grade sucrose source, the non-food-grade maltose source. $MgSO_4$. $MgSO_4$. $FeSO_4$, $KH_2PO_4$. NaCl, $CaCl_2$, and yeast extract.

19. The method of any of statements 1-18, further comprising incubating the fermentation mixture under conditions sufficient to generate a composition comprising maltosyl-isomaltooligosaccharide with a mass average molecular weight distribution of about 650 to 1000 daltons, or 650 to 1500 daltons, or 650-2000 daltons 20. The method of any of statements 1-19, where the conditions comprise a temperature, pH, and a time of fermentation sufficient to generate a composition comprising maltosyl-isomaltooligosaccharide with a mass average molecular weight distribution of about 650 to 1000 daltons.

21. The method of any of statements 1-20, comprising incubating the fermentation mixture at a pH of 4 to 8.

22. The method of any of statements 1-21, comprising incubating the fermentation mixture at a pH of 4.5 to 7.0, or a pH of 4.75 to 6.5, or a pH of 5.0 to 6.0, or a pH of 5.5.

23. The method of any of statements 1-22, comprising adding alkali to maintain the fermentation mixture pH.

24. The method of any of statements 1-23, comprising incubating the fermentation mixture at a temperature of about 10° C. to about 50° C., or from about 15° C. to about 45° C., or from about 20° C. to about 40° C., or from about 22° C. to about 37° C., or from about 23° C. to about 33° C., or from about 25° C. to about 30° C., or at about 27° C. to about 29° C.

25. The method of any of statements 1-24, comprising incubating the fermentation mixture at a temperature of about 28° C.

26. The method of any of statements 1-25, comprising incubating the fermentation mixture for a time sufficient to generate a composition comprising maltosyl-isomaltooligosaccharide with a mass average molecular weight distribution of about 650 to 1500 daltons.

27. The method of any of statements 1-26, comprising incubating the fermentation mixture for about 20 to about 120 hours.

28. The method of any of statements 1-27, comprising incubating the fermentation mixture for about 25 to about 100 hours, or about 30 to about 90 hours, or about 35 to about 80 hours, or about 40 to about 70 hours.

29. The method of any of statements 1-28, comprising incubating the fermentation mixture indefinitely while adding at least one of the sucrose and the maltose to the fermentation mixture and removing maltosyl-isomaltooligosaccharide therefrom.

30. The method of any of statements 1-29, where the composition comprises a mass average molecular weight distribution of about 730 to 900 daltons.

31. The method of any of statements 1-30, where the maltosyl-isomaltooligosaccharides contain more α-(1-6) glucosyl linkages than α-(1,2), α-(1,3), or α-(1,4) glucosyl linkages.

32. The method of any of statements 1-31, where the maltosyl-isomaltooligosaccharides contain 1-3 branches.

33. The method of any of statements 1-32, where the maltosyl-isomaltooligosaccharides contain 1-3 branches selected from α-(1,2), α-(1,3), or α-(1,4) glucosyl linkage branches.

34. The method of any of statements 1-33, where the composition comprises a mixture of oligosaccharides and at least 50% of the oligosaccharides have α-(1,6) glucosyl linkages, or at least 52% of the oligosaccharides have α-(1,6) glucosyl linkages, or at least 55% of the oligosaccharides have α-(1,6) glucosyl linkages, or at least 60% of the oligosaccharides have α-(1,6) glucosyl linkages, or at least 65% of the oligosaccharides have α-(1,6) glucosyl linkages, or at least 70% of the oligosaccharides have α-(1,6) glucosyl linkages, or at least 75% of the oligosaccharides have α-(1,6) glucosyl linkages, or at least 80% of the oligosaccharides have α-(1,6) glucosyl linkages, or at least 85% of the oligosaccharides have α-(1,6) glucosyl linkages, or at least 87% of the oligosaccharides have α-(1,6) glucosyl linkages, or at least 89% of the oligosaccharides have α-(1,6) glucosyl linkages, or at least 90% of the oligosaccharides have α-(1,6) glucosyl linkages.

35. The method of any of statements 1-34, where each maltosyl-isomaltooligosaccharide in the composition has at least one alpha-(1,4) glucosyl linkage.
36. The method of any of statements 1-35, where the maltosyl-isomaltooligosaccharides in the composition comprise one or more α-(1,4) glucosyl linkages, or one or more α-(1,2) glucosyl linkages, or one or more α-(1,3) glucosyl linkages.
37. The method of any of statements 1-36, where the maltosyl-isomaltooligosaccharides in the composition can optionally have one [—O-α-(1,4)-] linkage at the reducing end.
38. The method of any of statements 1-37, where the maltosyl-isomaltooligosaccharides have no more than about 40 glucose units, no more than about 35 glucose units, no more than about 30 glucose units, no more than about 28 glucose units, no more than about 25 glucose units, no more than about 23 glucose units, no more than about 20 glucose units, no more than about 18 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units as detected by HPAEC-PAD or HPLC-RID.
39. The method of any of statements 1-38, where the maltosyl-isomaltooligosaccharides have a maltose unit at the reducing end.
40. The method of any of statements 1-39, where the composition consists of less than 5%/brix glucose, or less than 4%/brix glucose, or less than 3%/brix glucose, or less than 2%/brix glucose, or less than 1%/brix glucose as detected by HPAEC-PAD or HPLC-RID.
41. The method of any of statements 1-40, where the composition has less than 5%/brix sucrose, or less than 4%/brix sucrose, or less than 3%/brix sucrose, as detected by HPAEC-PAD or HPLC-RID.
42. The method of any of statements 1-41, where the composition has less than 3%/brix fructose, or less than 2%/brix fructose, or less than 1%/brix fructose, or less than 0.5%/brix fructose, or less than 0.25%/brix fructose as detected by HPAEC-PAD or HPLC-RID.
43. The method of any of statements 1-42, where the composition has more than 7%/brix lactate, or more than 6%/brix lactate, or more than 5%/brix lactate, or more than 3%/brix lactate, or more than 2%/brix lactate, or more than 1%/brix lactate, as detected by HPAEC-PAD or HPLC-RID.
44. The method of any of statements 1-43, where the composition has less than 6%/brix maltose, or less than 5%/brix maltose, or less than 4%/brix maltose, as detected by HPAEC-PAD or HPLC-RID.
45. The method of any of statements 1-44, where the composition has more than 10%/brix mannitol, or more than 12%/brix mannitol, or more than 15%/brix mannitol as detected by HPAEC-PAD or HPLC-RID.
46. The method of any of statements 1-45, where the composition has less than 30%/brix mannitol, or less than 20%/brix mannitol, or less than 15% mannitol as detected by HPAEC-PAD or HPLC-RID.
47. The method of any of statements 1-46, where the composition has the compositions less than 4%/brix glycerol, or less than 3%/brix glycerol, or less than 2%/brix glycerol, or less than 1%/brix glycerol, or less than 0.5%/brix glycerol detectable by HPLC-RID or HPLC-RID.
48. The method of any of statements 1-47, where the composition has the compositions more than 0.01%/brix formic acid, or more than 0.02%/brix formic acid, or more than 0.03%/brix formic acid, or more than 0.04%/brix glycerol detectable by HPLC-RID or HPLC-RID.
49. The method of any of statements 1-48, where the composition has less than 20%/brix MIMO-DP3, or less than 19%/brix MIMO-DP3, or less than 18%/brix MIMO-DP3, or less than 17%/brix MIMO-DP3, or less than 16%/brix MIMO-DP3, or less than 15%/brix MIMO-DP3.
50. The method of any of statements 1-49, where the composition has less than 30%/brix MIMO-DP4, or less than 25%/brix MIMO-DP4, or less than 20%/brix MIMO-DP4, or less than 15%/brix MIMO-DP4, or less than 12%/brix MIMO-DP4.
51. The method of any of statements 1-50, where the composition has more than 5%/brix MIMO-DP5, or more than 6%/brix MIMO-DP5, or more than 7%/brix MIMO-DP5, or more than 8%/brix MIMO-DP5, or more than 9%/brix MIMO-DP5.
52. The method of any of statements 1-51, where the composition has more than 3%/brix MIMO-DP6, or more than 4%/brix MIMO-DP6, or more than 5%/brix MIMO-DP6, or more than 6%/brix MIMO-DP6.
53. The method of any of statements 1-52, where the composition has more than 1%/brix MIMO-DP7, or more than 2%/brix MIMO-DP7, or more than 2.5%/brix MIMO-DP7, or more than 2.75%/brix MIMO-DP7.
54. The method of any of statements 1-53, where the composition has more than 0.5%/brix MIMO-DP8, or more than 1%/brix MIMO-DP8, or more than 1.5%/brix MIMO-DP8.
55. The method of any of statements 1-54, where the composition has at least 3%, or at least 4%, or at least 5%, or at least 6% of one or more maltodextrins.
56. A composition comprising the maltosyl-isomaltooligosaccharides with a mass average molecular weight distribution of about 650 to 2000 daltons, at least 4% of one or more maltodextrins, and more than 1%/brix lactate, as detected by HPAEC-PAD or HPLC-RID.
57. The composition of statement 56, with more than 7%/brix lactate, or more than 6%/brix lactate, or more than 5%/brix lactate, or more than 3%/brix lactate, or more than 2%/brix lactate.
58. The composition of statement 56 or 57, where the mass average molecular weight distribution of the maltosyl-isomaltooligosaccharides is about 730 to 900 daltons.
59. The composition of any of statements 56, 57, or 58, where the maltosyl-isomaltooligosaccharides contain more α-(1-6) glucosyl linkages than α-(1,2), α-(1.3), or α-(1,4) glucosyl linkages.
60. The composition of any of statements 56-59, where the composition comprises a mixture of oligosaccharides and at least 50% of the oligosaccharides have α-(1,6) glucosyl linkages, or at least 52% of the oligosaccharides have α-(1,6) glucosyl linkages, or at least 55% of the oligosaccharides have α-(1,6) glucosyl linkages, or at least 60% of the oligosaccharides have α-(1,6) glucosyl linkages, or at least 65% of the oligosaccharides have α-(1,6) glucosyl linkages, or at least 70% of the oligosaccharides have α-(1,6) glucosyl linkages, or at least 75% of the oligosaccharides have α-(1,6) glucosyl linkages, or at least 80% of the oligosaccharides have α-(1,6) glucosyl linkages, or at least 85% of the oligosaccharides have α-(1,6) glucosyl linkages, or at least 87% of the oligosaccharides have α-(1,6) glucosyl linkages, or at least 89% of the oligosaccharides have α-(1,6) glucosyl linkages, or at least 90% of the oligosaccharides have α-(1,6) glucosyl linkages.

61. The composition of any of statements 58-60, where each maltosyl-isomaltooligosaccharide in the composition has at least one alpha-(1,4) glucosyl linkage.

62. The composition of any of statements 58-61, where the maltosyl-isomaltooligosaccharides in the composition comprise one or more α-(1,4) glucosyl linkages, or one or more α-(1,2) glucosyl linkages, or one or more α-(1.3) glucosyl linkages.

63. The composition of any of statements 58-62, where the maltosyl-isomaltooligosaccharides in the composition can optionally have one [—O-α-(1,4)-] linkage at the reducing end.

64. The composition of any of statements 58-63, where the maltosyl-isomaltooligosaccharides contain 1-3 branches.

65. The composition of any of statements 58-64, where the maltosyl-isomaltooligosaccharides contain 1-3 branches selected from α-(1,2), α-(1,3), or α-(1,4) glucosyl linkage branches.

66. The composition of any of statements 58-65, where the maltosyl-isomaltooligosaccharides have no more than about 40 glucose units, no more than about 35 glucose units, no more than about 30 glucose units, no more than about 28 glucose units, no more than about 25 glucose units, no more than about 23 glucose units, no more than about 20 glucose units, no more than about 18 glucose units, or no more than about 16 glucose units, or no more than about 15 glucose units, or no more than about 14 glucose units, or no more than about 13 glucose units, or no more than about 12 glucose units, or no more than about 11 glucose units, or no more than about 10 glucose units as detected by HPAEC-PAD or HPLC-RID.

67. The composition of any of statements 58-66, where the maltosyl-isomaltooligosaccharides have a maltose unit at the reducing end.

68. The composition of any of statements 58-67, where the composition consists of less than 5%/brix glucose, or less than 4%/brix glucose, or less than 3%/brix glucose, or less than 2%/brix glucose, or less than 1%/brix glucose as detected by HPAEC-PAD or HPLC-RID.

69. The composition of any of statements 58-68, where the composition has less than 5%/brix sucrose, or less than 4%/brix sucrose, or less than 3%/brix sucrose, as detected by HPAEC-PAD or HPLC-RID.

70. The composition of any of statements 58-69, where the composition has less than 3%/brix fructose, or less than 2%/brix fructose, or less than 1%/brix fructose, or less than 0.5%/brix fructose, or less than 0.25%/brix fructose as detected by HPAEC-PAD or HPLC-RID.

71. The composition of any of statements 58-70, where the composition has less than 6%/brix maltose, or less than 5%/brix maltose, or less than 4%/brix maltose, as detected by HPAEC-PAD or HPLC-RID.

72. The composition of any of statements 58-71, where the composition has more than 10%/brix mannitol, or more than 12%/brix mannitol, or more than 15%/brix mannitol as detected by HPAEC-PAD or HPLC-RID.

73. The composition of any of statements 58-72, where the composition has less than 30%/brix mannitol, or less than 20%/brix mannitol, or less than 15% mannitol, or less than 10%/brix mannitol, or less than 5% mannitol, or less than 2%/brix mannitol, or less than 1% mannitol as detected by HPAEC-PAD or HPLC-RID.

74. The composition of any of statements 58-73, where the composition has the compositions less than 4%/brix glycerol, or less than 3%/brix glycerol, or less than 2%/brix glycerol, or less than 1%/brix glycerol, or less than 0.5%/brix glycerol detectable by HPLC-RID or HPLC-RID.

75. The composition of any of statements 58-74, where the composition has the compositions more than 0.01%/brix formic acid, or more than 0.02%/brix formic acid, or more than 0.03%/brix formic acid, or more than 0.04%/brix glycerol detectable by HPLC-RID or HPLC-RID.

76. The composition of any of statements 58-75, where the composition has less than 20%/brix MIMO-DP3, or less than 19%/brix MIMO-DP3, or less than 18%/brix MIMO-DP3, or less than 17%/brix MIMO-DP3, or less than 16%/brix MIMO-DP3, or less than 15%/brix MIMO-DP3.

77. The composition of any of statements 58-76, where the composition has less than 30%/brix MIMO-DP4, or less than 25%/brix MIMO-DP4, or less than 20%/brix MIMO-DP4, or less than 15%/brix MIMO-DP4, or less than 12%/brix MIMO-DP4.

78. The composition of any of statements 58-77, where the composition has more than 5%/brix MIMO-DP5, or more than 6%/brix MIMO-DP5, or more than 7%/brix MIMO-DP5, or more than 8%/brix MIMO-DP5, or more than 9%/brix MIMO-DP5.

79. The composition of any of statements 58-78, where the composition has more than 3%/brix MIMO-DP6, or more than 4%/brix MIMO-DP6, or more than 5%/brix MIMO-DP6, or more than 6%/brix MIMO-DP6.

80. The composition of any of statements 58-79, where the composition has more than 1%/brix MIMO-DP7, or more than 2%/brix MIMO-DP7, or more than 2.5%/brix MIMO-DP7, or more than 2.75%/brix MIMO-DP7.

81. The composition of any of statements 58-80, where the composition has more than 0.5%/brix MIMO-DP8, or more than 1%/brix MIMO-DP8, or more than 1.5%/brix MIMO-DP8.

82. The composition of any of statements 58-81, further comprising at least 3%, or at least 4%, or at least 5%, or at least 6% of one or more maltodextrins.

83. The composition of any of statements 58-82, further comprising at least 1%, or at least 2%, or at least 3%, or at least 4% panose.

84. A composition made by the method of any of statements 1-57.

85. A composition with the following components:

| Component | |
|---|---|
| brix | 16.00 |
| mannitol | 0.07 |
| glucose | 0.44 |
| fructose | 9.79 |
| leucrose | 3.01 |
| sucrose | 0.98 |

-continued

| Component | |
|---|---|
| maltose | 0.84 |
| MIMO-DP3 | 2.72 |
| MIMO-DP4 | 4.50 |
| MIMO-DP5 | 4.51 |
| MIMO-DP6 | 4.46 |
| MIMO-DP7 | 3.83 |
| MIMO-DP8 | 4.02 |
| MIMO-DP9 | 3.34 |
| MIMO-DP10 | 4.93 |
| MIMO-DP11 | 3.39 |
| MIMO-DP12 | 2.98 |
| MIMO-DP13 | 2.93 |
| MIMO-DP14 | 2.55 |
| MIMO-DP15 | 2.18 |
| MIMO-DP16 | 1.37 |
| MIMO-DP17 | 1.06 |
| MIMO-DP18 | 1.38 |
| MIMO-DP19 | 1.17 |
| MIMO-DP20 | 0.64 |
| MIMO-DP21 | 0.67 |
| MIMO-DP22 | 0.79 |
| MIMO-DP23 | 0.66 |
| lactic acid | 20.58 |
| glycerol | 1.04 |
| formic acid | 0.00 |
| acetic acid | 1.04 |
| ethanol | 8.15 |
| MIMO, tot: | 54.06 |
| Total: | 100.00 |
| Purity, %: | 54.06 |
| MWD, Da: | 1619.2 |

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "an oligosaccharide" or "a maltose" includes a plurality of such compounds, oligosaccharides, or maltose sugars, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A method comprising:
    (a) contacting dextransucrase-producing bacterial cells with an aqueous culture medium comprising a ratio of sucrose to maltose ranging from 2.0 to about 4.5 to form a fermentation mixture, where at least one source of the sucrose and the maltose in the fermentation mixture is an impure source of sucrose or maltose; and
    (b) fermenting the fermentation mixture for a time and under conditions to generate a composition comprising maltosyl-isomaltooligosaccharides (MIMOs) with a mass average molecular weight distribution of about 650 to 2000 daltons.

2. The method of claim 1, where the sucrose comprises raw sugar, molasses, sugar cane syrup, sweet sorghum, energy cane syrup, beet sugar, beet molasses, sugar beet greens, maple syrup, algae, or any combinations thereof.

3. The method of claim 1, where the maltose is, or is derived from, maltose syrup, high maltose syrup, malt, saccharified starch, corn/maize starch, potato starch, tapioca starch, wheat starch, oat starch, millet starch, sorghum starch, rice starch, arrowroot starch, taro starch, kudzu starch, yam starch, or any combination thereof.

4. The method of claim 1, where the impure source of sucrose or maltose does not contain toxic compounds, heavy metals, or toxic materials detectable by HPAEC-PAD, HPLC, ICP-MS, or HPLC-RID.

5. The method of claim 1, where the dextransucrase-producing bacterial cells are *Leuconostoc mesenteroides, Leuconostoc citreum, Leuconostoc gasicomitatum, Leuconostoc kimchi, Leuconostoc amelibiosum, Weissella confusa, Weissella cibaria, Lactococcus* spp., *Streptococcus mutans, Lactobacillis* spp. *Pediococcus pentosaceus* spp. or a mixture thereof.

6. The method of claim 1, where the composition further comprises at least 3% of one or more maltodextrins.

7. A composition comprising MIMOs with a mass average molecular weight distribution of about 650 to 2000 daltons and with a degree of polymerization ranging from about DP 3 to DP 30; sucrose; maltose; one or more maltodextrins; lactate; glycerol; and acetate.

8. The composition of claim 7, comprising MIMOs with a degree of polymerization ranging from DP 3 to DP 30; mannitol; glucose; sucrose; maltose; panose; 1,4-DP 3 oligosaccharide(s); 1,4-DP 4 oligosaccharide(s); lactate; glycerol; formate; and acetate.

9. The composition of claim 7, comprising composition 1 or composition 2 in the following table, where the values shown are given as %/brix, or % of refractive dry solids

|  | Composition 1 | Composition 2 |
| --- | --- | --- |
| brix: | 20.0 | 19.8 |
| mannitol | 10.26 | 24.08 |
| fructose | 0.56 | 0.08 |
| sucrose | 4.08 | 1.25 |
| maltose | 2.63 | 3.11 |
| MIMO-DP 3 | 12.04 | 8.79 |
| MIMO-DP 4 | 21.87 | 20.14 |
| 1,4-DP3 | 6.61 | 6.80 |
| MIMO-DP 5 | 13.41 | 13.96 |
| MIMO-DP 6 | 4.18 | 5.25 |
| MIMO-DP 7 | 1.63 | 2.14 |
| MIMO-DP 8 | 0.00 | 0.87 |
| 1,4-DP4 | 2.51 | 2.80 |
| MIMO-DP 9 | 0.00 | 0.00 |
| lactate | 4.23 | 10.79 |
| glycerol | 0.05 | 0.13 |
| formate | 0.00 | 0.02 |
| acetate | 1.69 | 4.10 |
| TOTAL: | 91.04 | 104.30 |
| MIMO, %: | 53.13 | 51.14 |
| Purity, %: | 58.36 | 49.03 |
| MWD: | 693.21 | 723.72 |
| Yield %: | 67.30 | 55.98 | where 1,4-DP3, and 1,4-DP4 are maltodextrins.

10. The composition of claim 7, comprising composition 3 in the following table, where the values shown are given as %/brix, or % of refractive dry solids

| Variable | Composition 3 |
| --- | --- |
| brix: | 18.7 |
| mannitol | 22.49 |
| fructose | 0.02 |
| sucrose | 1.03 |
| maltose | 2.99 |
| MIMO-DP 3 | 6.88 |
| MIMO-DP 4 | 14.07 |
| 1,4-DP3 | 6.29 |
| MIMO-DP 5 | 12.18 |
| MIMO-DP 6 | 5.90 |
| MIMO-DP 7 | 2.33 |
| MIMO-DP 8 | 1.04 |
| 1,4-DP4 | 5.02 |
| MIMO-DP 9 | 0.00 |
| lactate | 16.03 |
| glycerol | 0.35 |
| formate | 0.00 |
| acetate | 4.39 |
| TOTAL: | 101.52 |
| MIMO, %: | 42.40 |
| Purity, %: | 41.77 |
| MWD: | 745.47 |
| Yield %: | 45.76 | where 1,4-DP3, and 1,4-DP4 are maltodextrins.

11. The composition of claim 7, comprising composition 4 or composition 5 in the following table, where the values shown are given as %/brix, or % of refractive dry solids

| %/brix | Composition 4 | Composition 5 |
| --- | --- | --- |
| Brix | 25.5 | 26.2 |
| mannitol | 18.28 | 17.35 |
| glucose | 0.44 | 0.93 |
| fructose | 0.00 | 0.00 |
| sucrose | 2.93 | 2.84 |
| maltose | 1.95 | 2.72 |
| panose | 4.65 | 4.43 |
| MIMO-DP4 | 11.33 | 9.96 |
| 1,4-DP3 | 10.66 | 10.23 |
| MIMO-DP5 | 10.29 | 9.05 |
| MIMO-DP6 | 7.08 | 6.82 |
| MIMO-DP7 | 2.94 | 3.12 |
| MIMO-DP8 | 1.85 | 1.69 |
| 1,4-DP4 | 9.93 | 6.33 |
| MIMO-DP9 | 0.00 | 0.00 |
| MIMO-DP10 | 0.00 | 0.00 |
| lactic acid | 8.30 | 8.08 |
| glycerol | 0.24 | 0.23 |
| formic acid | 0.06 | 0.05 |
| acetic acid | 2.92 | 2.86 |
| MIMO | 38.15 | 35.07 |
| MO | 20.59 | 16.56 |
| Total | 93.86 | 86.70 |
| Purity | 40.64 | 40.45 |
| MWD | 795.82 | 790.16 |
| S/M | n/a | n/a. |

* * * * *